(12) United States Patent
Sugawara et al.

(10) Patent No.: US 11,203,025 B2
(45) Date of Patent: Dec. 21, 2021

(54) ELECTROSPINNING DEVICES AND SYSTEMS AND METHODS THEREOF

(71) Applicant: KAO CORPORATION, Tokyo (JP)

(72) Inventors: Hirokatsu Sugawara, Cincinnati, OH (US); Ryan Forsthoefel, Dayton, OH (US); David Mefford, Union Township, OH (US); Brian Umstead, Union Township, OH (US)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/655,577

(22) Filed: Oct. 17, 2019

(65) Prior Publication Data

US 2020/0122169 A1 Apr. 23, 2020

Related U.S. Application Data

(60) Provisional application No. 62/746,906, filed on Oct. 17, 2018.

(51) Int. Cl.

| | |
|---|---|
| *B05B 5/16* | (2006.01) |
| *D01D 5/00* | (2006.01) |
| *B05B 5/025* | (2006.01) |
| *B05B 5/08* | (2006.01) |
| *B05B 12/00* | (2018.01) |
| *B05B 11/00* | (2006.01) |
| *B05B 5/053* | (2006.01) |
| *B05B 12/12* | (2006.01) |

(52) U.S. Cl.
CPC ............ *B05B 5/1691* (2013.01); *B05B 5/025* (2013.01); *B05B 5/0538* (2013.01); *B05B 5/087* (2013.01); *B05B 11/00* (2013.01); *B05B 12/004* (2013.01); *D01D 5/0061* (2013.01); *B05B 12/124* (2013.01)

(58) Field of Classification Search
None
See application file for complete search history.

(56) References Cited

U.S. PATENT DOCUMENTS

| 5,222,664 A | 6/1993 | Noakes et al. |
|---|---|---|
| 6,311,903 B1 | 11/2001 | Gaw et al. |
| (Continued) | | |

FOREIGN PATENT DOCUMENTS

| JP | 9-504992 | 5/1997 |
|---|---|---|
| JP | 3857136 | 9/2006 |
| JP | 4415014 | 11/2009 |

OTHER PUBLICATIONS

International Search Report and Written Opinion dated Jan. 9, 2020, in PCT/US19/56723, citing documents AA-AB therein, 16 pages.

*Primary Examiner* — Binu Thomas
(74) *Attorney, Agent, or Firm* — Oblon, McClelland, Maier & Neustadt, L.L.P.

(57) ABSTRACT

A portable, hand-held electrospinning or electrospraying device and system, method, and portions thereof are described. Such device can be for electrospinning or electrospraying a predetermined solution toward a deposit surface. The device can have a durable portion, a semi-durable portion, and a consumable portion. The consumable portion can be received and held by the semi-durable portion, and the semi-durable portion holding the consumable portion can be removably coupled to the durable portion.

20 Claims, 24 Drawing Sheets

(56) References Cited

U.S. PATENT DOCUMENTS

| | | | |
|---|---|---|---|
| 6,318,647 B1* | 11/2001 | Gaw | B05B 5/1691 |
| | | | 239/690 |
| 7,823,808 B2 | 11/2010 | Yamaguchi et al. | |
| 7,959,597 B2 | 6/2011 | Baker et al. | |
| 2006/0100655 A1 | 5/2006 | Leong et al. | |
| 2007/0176029 A1* | 8/2007 | Yamaguchi | B05B 5/1691 |
| | | | 239/690 |
| 2011/0144588 A1 | 6/2011 | Taylor et al. | |
| 2014/0110492 A1* | 4/2014 | Cooper | B05B 5/087 |
| | | | 239/3 |
| 2017/0182264 A1 | 6/2017 | Pelkus | |
| 2017/0239094 A1 | 8/2017 | Dubson | |

\* cited by examiner

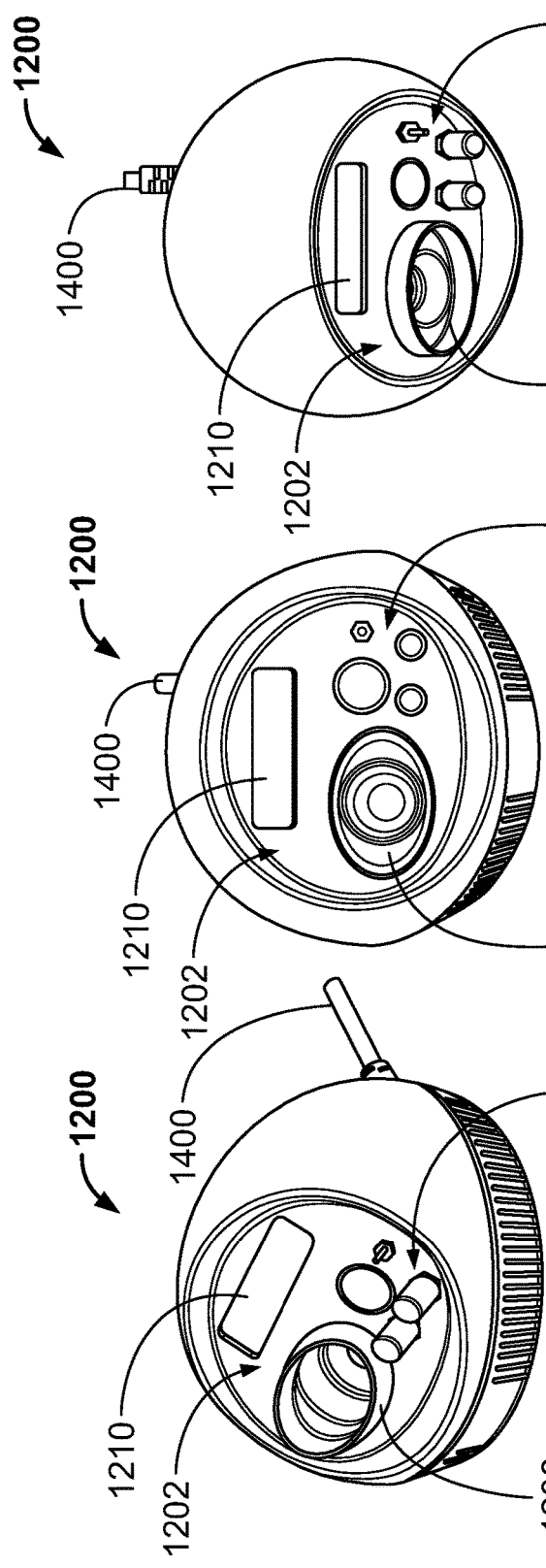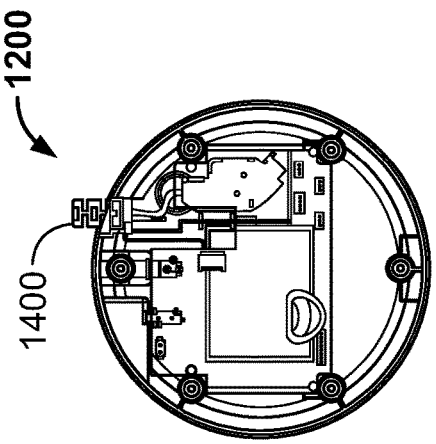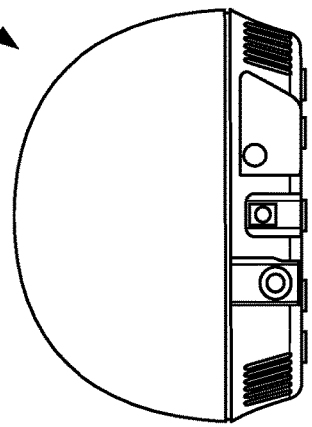

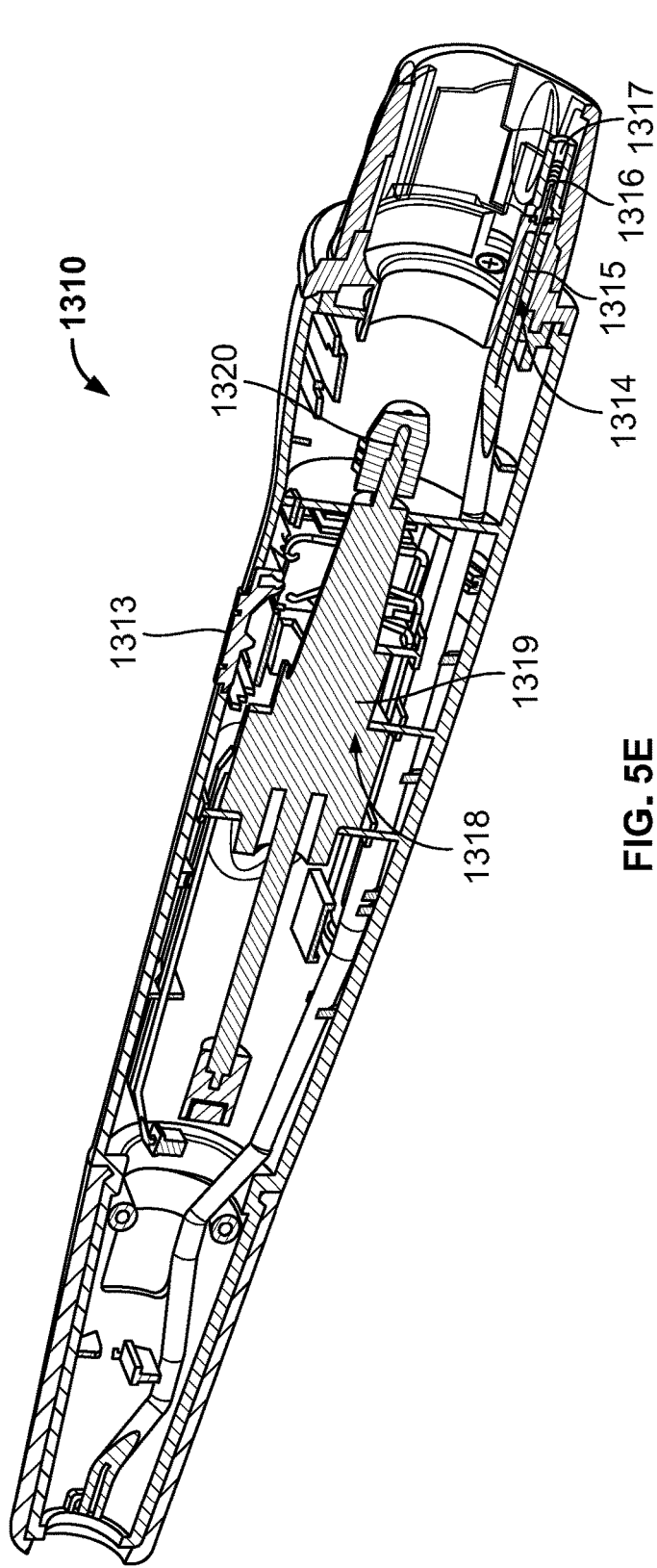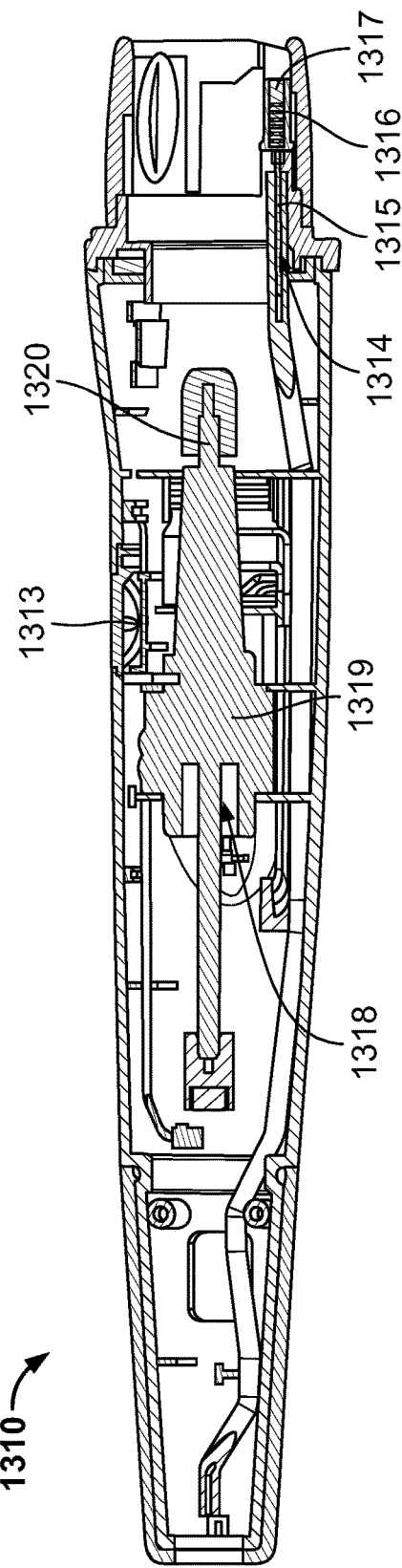
FIG. 5E
FIG. 5F

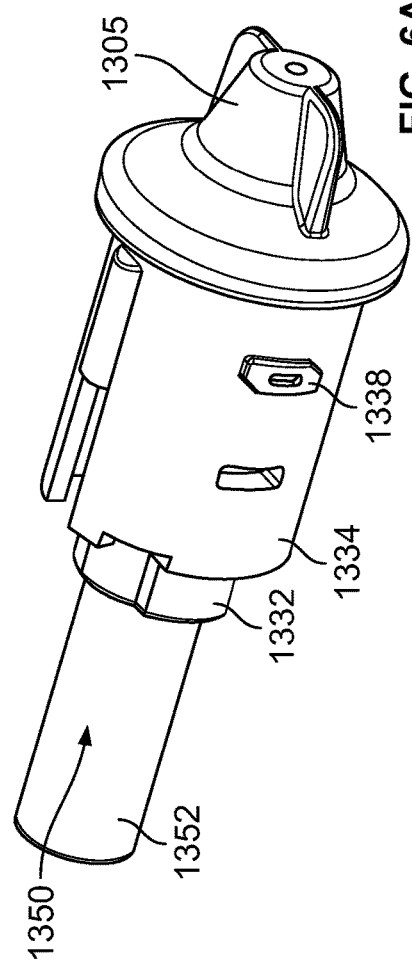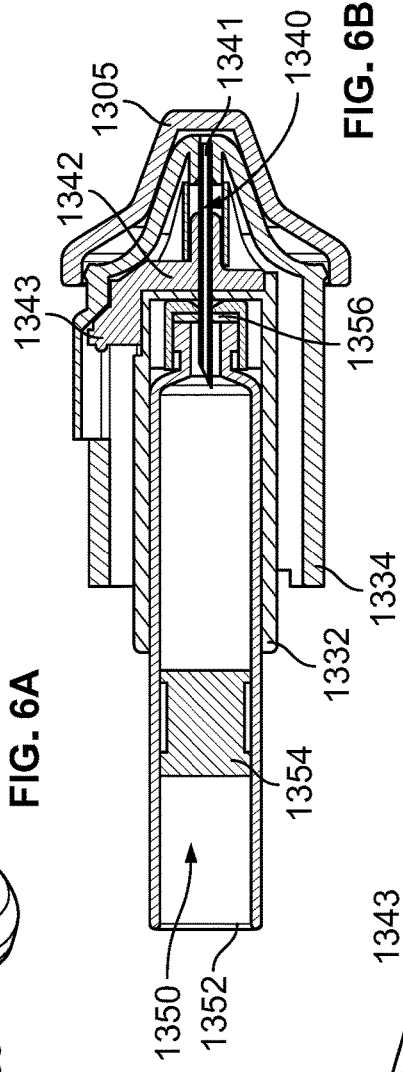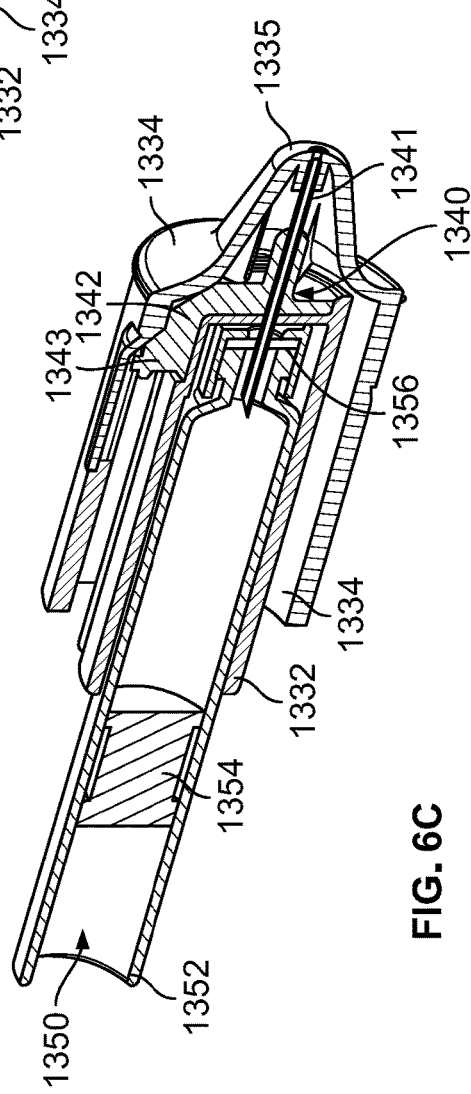

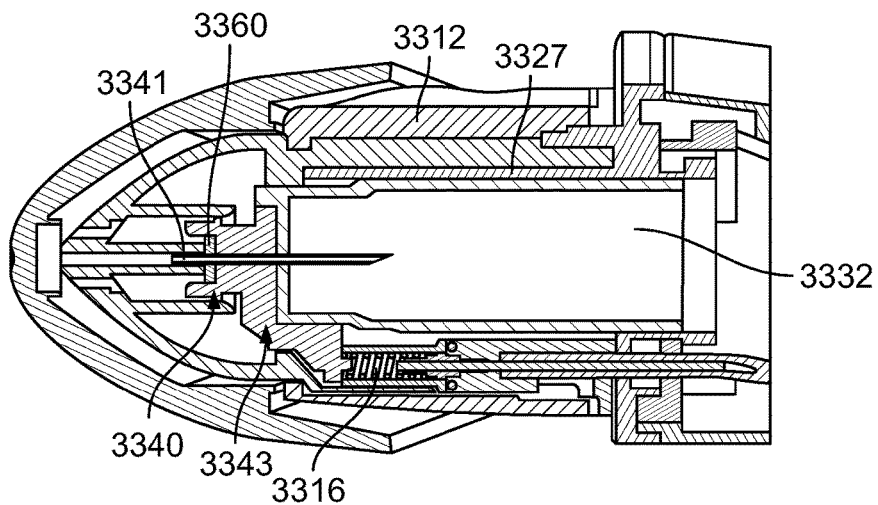
FIG. 18
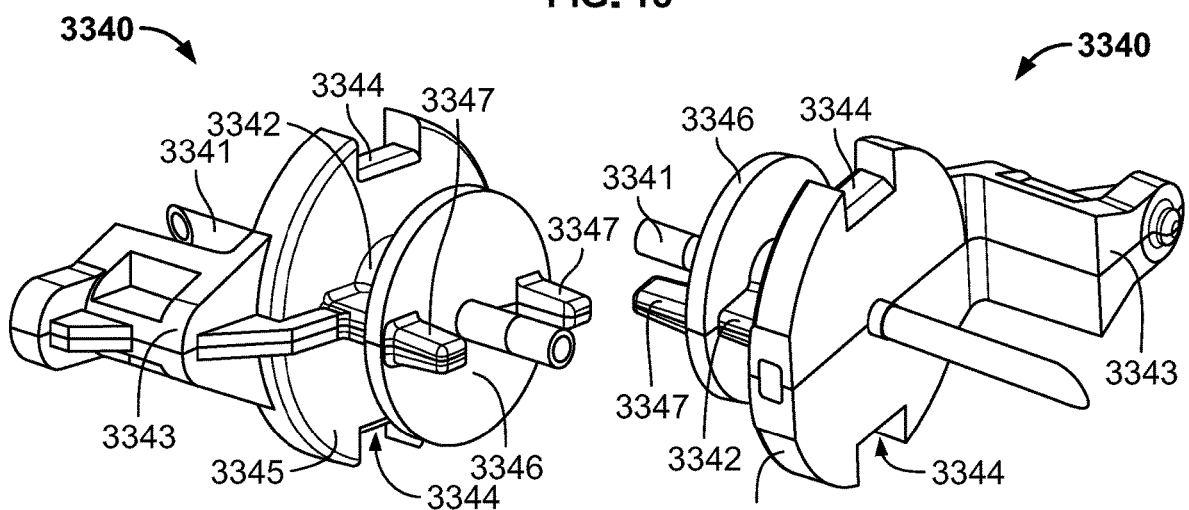
FIG. 19A
FIG. 19B
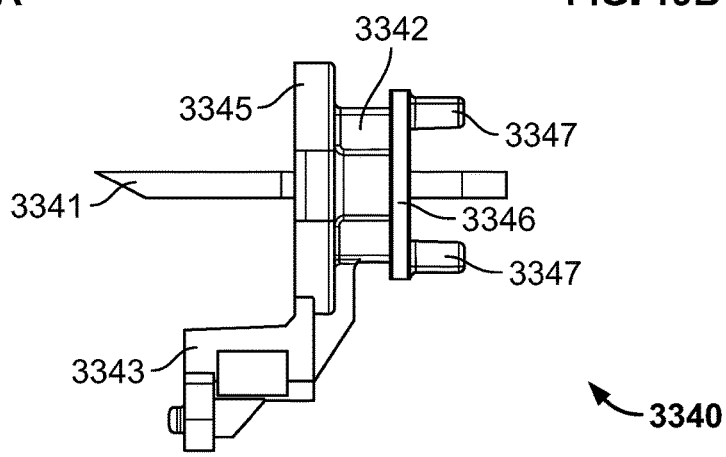
FIG. 19C

ELECTROSPINNING DEVICES AND SYSTEMS AND METHODS THEREOF

CROSS REFERENCE TO RELATED APPLICATION(S)

This application is based upon and claims benefit of priority from U.S. Provisional Patent Application 62/746,906, filed on Oct. 17, 2018, the entire contents of which are incorporated herein by reference.

FIELD

Embodiments of the disclosed subject matter are directed generally to electrospinning devices and systems and methods thereof. More particularly, embodiments of the disclosed subject matter are directed to portable, hand-held electrospinning devices and systems, methods, and portions thereof.

BACKGROUND

Conventional hand-held electrospraying or electrospinning devices may have a durable portion and a consumable portion containing the material for electrospraying or electrospinning. The consumable portion may be provided within the durable portion for operation of the electrospraying or electrospinning device. However, conventional hand-held electrospraying or electrospinning devices may not be provided with a so-called semi-durable portion configured to receive a consumable portion and be provided in a durable portion with the consumable portion, rather than the consumable portion being directly provided in the durable portion.

U.S. Pat. No. 6,311,903 ("the '903 patent") describes an electrostatic spraying device. The '903 patent describes that the electrostatic spraying device is designed to be portable, hand-held, self-containing, and battery-operated, with a disposable cartridge. According to the '903 patent, a disposable cartridge can be inserted into the electrostatic spraying device.

U.S. Pat. No. 7,823,808 ("the '808 patent") describes an electrospraying device. The '808 patent describes that the electrospraying device has a removable cartridge with a reservoir containing a volume of liquid compositions to be electrically sprayed on a user's skin, and that the device includes a nozzle for dispensing the liquid as well as an emitter electrode disposed adjacent to the nozzle for charging the liquid composition just being dispensed from the nozzle. A field electrode surrounds the reservoir in order to charge the liquid composition within the reservoir, which, according to the '808 patent, avoids an occurrence of electric current which would otherwise flow in the liquid composition and would deteriorate the composition remaining in the reservoir.

U.S. Patent App. Pub. No. 2017/0239094 ("the '094 publication") describes a portable electrospinning device. The '094 publication describes that the electrospinning device is handheld and for producing a electrospun fibrous mat. According to the '094 publication, the handheld device comprises a housing configured to be handheld by a user; a container accommodating at least one electrospinning medium; at least a nozzle in fluid communication with the container; a mechanism dispensing the medium from the container via said nozzle; an auxiliary electrode surrounding the nozzle; and a power supply providing electric potentials to the nozzle and the auxiliary electrode. The '094 publication also describes that the housing comprises an electrically conductive portion configured to be gripped by the user during operation, where the electrically conductive portion is connected to the power supply.

SUMMARY

According to one or more embodiments of the present disclosure, a portable, hand-held device for electrospinning or electrospraying a may be provided. The device can electrospin or electrospray a predetermined solution formulated for the device toward a deposit surface. The hand-held device may be comprised of a durable portion, a semi-durable portion, and a consumable portion. The consumable portion can be removably coupled to the semi-durable portion, and the semi-durable portion can be removably coupled to the durable portion. The durable portion can be configured to provide a high voltage to the semi-durable portion and can include a drive mechanism configured to cause the solution within a container of the consumable portion to be output to at least one electrode of the semi-durable portion, and a user control interface configured to receive manual input from a user to control the drive mechanism and application of the high voltage to the at least one electrode to create an electric field for application to the solution to electrospin or electrospray the solution from a nozzle of the semi-durable portion toward a deposit surface. The semi-durable portion can be configured to provide the high voltage to the at least one electrode and can include the nozzle, which is configured to output the solution from a nozzle tip thereof, and the at least one electrode, which is inside the nozzle. The consumable portion can include the container, which can be configured to contain a predetermined maximum volume of the solution and output the solution to the at least one electrode of the semi-durable portion.

Optionally, the consumable portion of the hand-held device, which may contain the solution to be output in electrospin or electrospray fashion, may be replaced in whole or in part to provide additional or alternative solution. Additionally or optionally, the semi-durable portion may be removed and replaced with another semi-durable portion configured to receive a consumable portion of a different configuration as compared to the consumable portion for the initial semi-durable portion. A base station may also be provided, and can output high voltage and communication signals to the hand-held device to enable the electrospin or electrospray operation by the hand-held device.

According to one or more embodiments, an electrospinning or electrospraying device can comprise: means for providing high voltage; means for generating an electric field and applying the electric field to solution based on the high voltage; means for outputting the solution to receive application of the electric field; means for outputting the solution as electrospun or electrosprayed solution; and means for controlling the means for generating the electric field and the means for outputting the solution as the electrospun or electrosprayed solution. Optionally, the device can be comprised of a means for replacing, means for locking a durable portion to a semi-durable portion, and/or means for locking a consumable portion that houses the solution to the semi-durable portion.

According to one or more embodiments, a portable, hand-held device for electrospinning or electrospraying toward a deposit surface a predetermined solution formulated for the device, can comprise a durable portion; and a semi-durable portion configured to removably receive therein a consumable portion, wherein the semi-durable portion is configured to be removably coupled to the durable portion, wherein the durable portion is configured to provide a high voltage to the semi-durable portion and includes: a user control interface configured to receive manual input from a user to control a drive mechanism and application of the high voltage to at least one electrode to create an electric field for application to the solution to electrospin or electrospray the solution from a nozzle of the semi-durable portion toward the deposit surface, wherein the semi-durable portion is configured to provide the high voltage to the at least one electrode and includes: the nozzle, which is configured to output the solution from a nozzle tip thereof, and the at least one electrode, which is inside the nozzle, wherein the at least one electrode includes: a hollow tube, a conductive body portion surrounding the hollow tube such that a portion of the hollow tube extends from a first side of the conductive body portion, wherein the conductive body portion forms at least one secondary electrode, and wherein a second side of the conductive body opposite the first side corresponds to an outward-facing side of a second planar portion, the second side having one or more projections extending therefrom.

One or more embodiments can also include or involve a portable, hand-held device for electrospinning or electrospraying toward a deposit surface a predetermined solution formulated for the device, the device comprising: a durable portion; and a semi-durable portion configured to removably receive therein a consumable portion, wherein the semi-durable portion is configured to be removably coupled to the durable portion, wherein the durable portion is configured to provide a high voltage to the semi-durable portion and includes: a user control interface configured to receive manual input from a user to control a drive mechanism and application of the high voltage to at least one electrode to create an electric field for application to the solution to electrospin or electrospray the solution from a nozzle of the semi-durable portion toward the deposit surface, wherein the semi-durable portion is configured to provide the high voltage to the at least one electrode and includes: the nozzle, which is configured to output the solution from a nozzle tip thereof, and the at least one electrode, which is inside the nozzle, and wherein part of the consumable portion overlaps the semi-durable portion in a side view of the device.

And embodiments of the disclosed subject matter can include or involve a portable, hand-held device for electrospinning or electrospraying toward a deposit surface a predetermined solution formulated for the device, the device comprising: a durable portion; and a semi-durable portion configured to removably receive therein a consumable portion, wherein the semi-durable portion is configured to be removably coupled to the durable portion, wherein the durable portion is configured to provide a high voltage to the semi-durable portion and includes: wherein the durable portion is configured to provide a high voltage to the semi-durable portion and includes: a user control interface configured to receive manual input from a user to control a drive mechanism and application of the high voltage to at least one electrode to create an electric field for application to the solution to electrospin or electrospray the solution from a nozzle of the semi-durable portion toward the deposit surface, wherein the semi-durable portion is configured to provide the high voltage to the at least one electrode and includes: the nozzle, which is configured to output the solution from a nozzle tip thereof, and wherein the coupling of the semi-durable portion to the durable portion includes a combined electrical and mechanical connection including a connection rod extending from an end of the durable portion and into the semi-durable portion, the connection rod having an end thereof coupled to an elastic member.

Embodiments can also include methods of providing, making, and/or using devices and systems, or portions thereof, according to embodiments of the disclosed subject matter. For example, using devices or systems according to one or more embodiments of the disclosed subject matter can involve providing a spraying or spinning formulation for the solution, where the spraying or spinning formulation may be comprised of a volatile solvent selected from alcohol and ketone, polymer, and water.

BRIEF DESCRIPTION OF THE DRAWINGS

The accompanying drawings, which are incorporated in and constitute a part of the specification, are illustrative of one or more embodiments of the disclosed subject matter, and, together with the description, explain various embodiments of the disclosed subject matter. Further, the accompanying drawings have not necessarily been drawn to scale, and any values or dimensions in the accompanying drawings are for illustration purposes only and may or may not represent actual or preferred values or dimensions. Where applicable, some or all select features may not be illustrated to assist in the description and understanding of underlying features.

FIG. 1 is a diagram of a system according to one or more embodiments of the disclosed subject matter.

FIG. 2A is a perspective view of a system according to one or more embodiments of the disclosed subject matter.

FIG. 2B is a sectional view of the system of FIG. 2A.

FIGS. 3A-3F show various views of a base station of the system of FIG. 2A.

FIG. 4A is a perspective view of a hand-held device of the system of FIG. 2A with a cap.

FIGS. 4B-4F show various views of the hand-held device of FIG. 2A.

FIG. 4G is an enlarged perspective sectional view of an end portion of the hand-held device of FIG. 4B.

FIG. 4H is an enlarged side sectional view of the end portion of the hand-held device of FIG. 4B.

FIGS. 5A-5D show various views of a durable portion of the hand-held device of FIG. 4A.

FIG. 5E is a perspective sectional view of the durable portion of the hand-held device of FIG. 5A.

FIG. 5F is a side sectional view of the durable portion of the hand-held device of FIG. 5A.

FIG. 5G is an enlarged sectional view of the durable portion of the hand-held device of FIG. 5A.

FIGS. 6A-6C show various views of a semi-durable portion and a consumable portion according to one or more embodiments of the disclosed subject matter.

FIGS. 7A-7C show various views of the semi-durable portion of FIGS. 6A-6C.

FIGS. 8A-8C show aspects of the semi-durable portion of FIGS. 7A-7C.

FIG. 9 is sectional view of a consumable portion according to one or more embodiments of the disclosed subject matter.

FIG. 10 is an exploded view of the semi-durable portion of FIGS. 7A-7C, particularly showing the interchangeability of different consumable portion housings or holders for the semi-durable portion.

FIG. 11 is an exploded view of a semi-durable portion and a consumable portion according to one or more embodiments of the disclosed subject matter, particularly showing the interchangeability of different consumable portion housings or holders of the semi-durable portion and respective consumable portions.

FIG. 18 is a side sectional view of an end portion of a hand-held device according to embodiments of the disclosed subject matter.

FIGS. 19A-19C show various views of an electrode according to embodiments of the disclosed subject matter.

DETAILED DESCRIPTION

Figure 1:
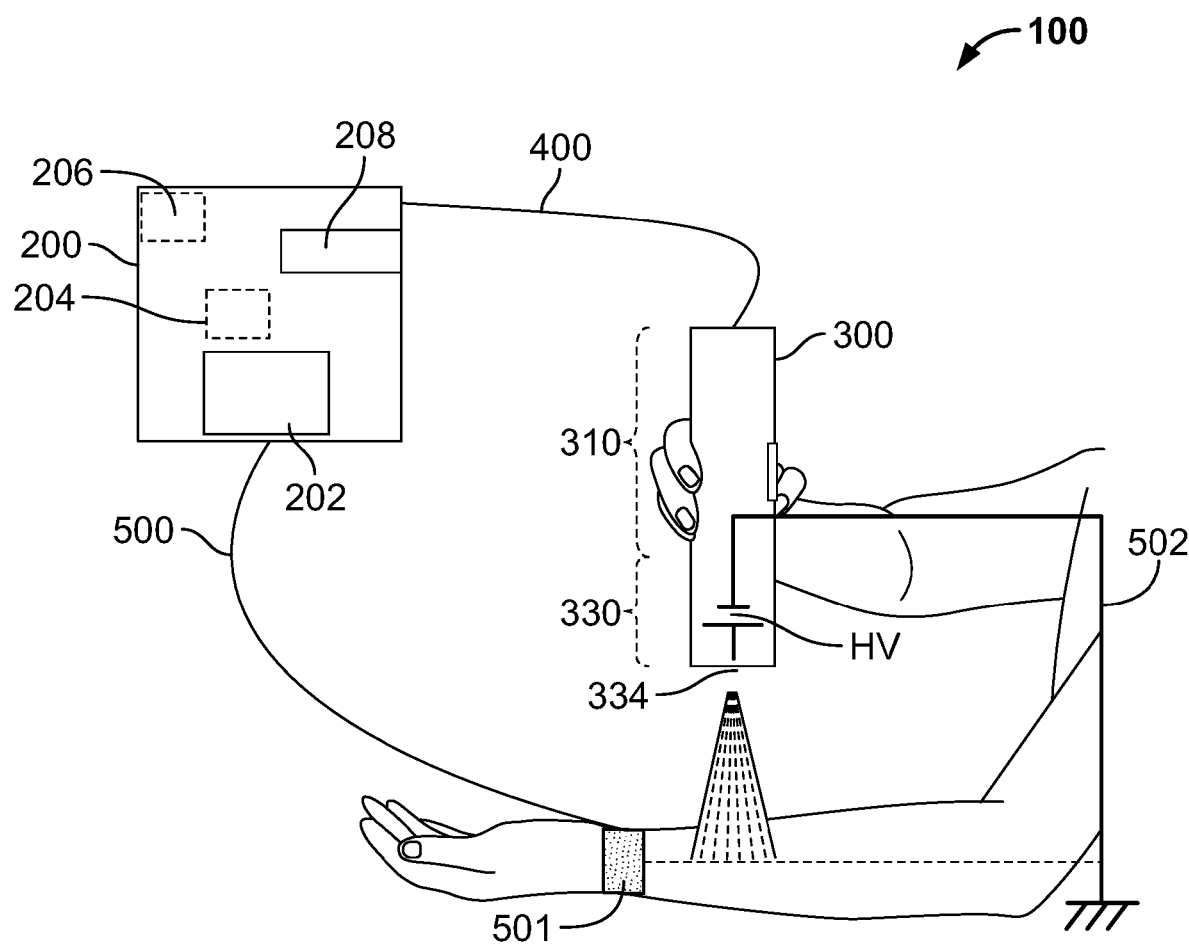

The description set forth below in connection with the appended drawings is intended as a description of various embodiments of the described subject matter and is not necessarily intended to represent the only embodiment(s). In certain instances, the description includes specific details for the purpose of providing an understanding of the described subject matter. However, it will be apparent to those skilled in the art that embodiments may be practiced without these specific details. In some instances, structures and components may be shown in block diagram form in order to avoid obscuring the concepts of the described subject matter. Wherever possible, the same reference numbers will be used throughout the drawings to refer to the same or the like parts.

Any reference in the specification to "one embodiment" or "an embodiment" means that a particular feature, structure, characteristic, operation, or function described in connection with an embodiment is included in at least one embodiment. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments, and it is intended that embodiments of the described subject matter can and do cover modifications and variations of the described embodiments.

It must also be noted that, as used in the specification, appended claims and abstract, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the described subject matter to any particular orientation or configuration. Furthermore, terms such as "first," "second," "third," etc. merely identify one of a number of portions, components, points of reference, operations and/or functions as described herein, and likewise do not necessarily limit embodiments of the described subject matter to any particular configuration or orientation.

Embodiments of the disclosed subject matter are directed generally to electrospraying or electrospinning devices and systems and methods thereof. More preferably, embodiments of the disclosed subject matter are directed to portable, hand-held electrospinning or electrospraying devices and systems, methods, and portions thereof. In that embodiments of the disclosed subject matter can involve portable, hand-held electrospinning or electrospraying devices and systems, methods, and portions thereof, such embodiments may be used in a clinical, salon, or at-home setting.

Generally speaking, electrospinning, which may be referred to as electric-field spinning, involves generating an electric field (EF) in and around a solution, for instance, a polymer solution, to draw out the solution to create relatively a fine fiber. The high voltage must be sufficiently high to generate an electric field sufficient to produce a Taylor cone. A plurality of such fibers may form a mesh or web on a surface, such as skin, for instance. The fiber diameter may be as small as a nanometer, for instance.

The flow rate of the output solution may be about 0.17 ml/min, preferably about 0.01 to about 1.0 ml/min, more preferably about 0.02 to about 0.5 ml/min, and most preferably about 0.03 to about 0.3 ml/min. Further, the flow rate may be caused or set based on current and voltage supplied to create the electric field, and desired fiber or droplet properties to be output. The flow rate may also be dependent upon characteristics of the solution, such as molecular weight, type, conductivity; environmental aspects, such as ambient temperature and/or ambient humidity; and apparatus configuration, such as the configuration of the nozzle.

One or more embodiments of the disclosed subject matter can involve application of a cosmetic, such as a base/foundation, a concealer, a moisturizer, or coloring. Of course, embodiments of the disclosed subject matter are not limited to application of cosmetics. For example, one or more embodiments of the disclosed subject matter can involve application of deodorants, scents, sun protection, creams, topical drug delivery, anti-microbial barriers and coatings, hydrophobic/phallic surface treatments, anti-fouling coatings, tissue repair, etc.

In general, embodiments of the disclosed subject matter can involve a portable, hand-held device for electrospinning or electrospraying a predetermined solution toward a deposit surface. The device can have a durable portion, a semi-durable portion, and a consumable portion. The consumable portion can be received and held by the semi-durable portion, and the semi-durable portion holding the consumable portion can be removably coupled to the durable portion.

The consumable portion can be removed from the semi-durable portion and replaced with a new consumable portion, for instance, when the initial consumable portion is out of solution or when there is a desire to switch to a consumable portion with a different solution. In one or more embodiments of the disclosed subject matter, a portion of the semi-consumable portion, for instance, a consumable portion housing of the semi-durable portion, may be removed from the semi-durable portion and replaced with a different (e.g., larger) consumable portion housing configured to receive and hold a different (e.g., larger) consumable portion.

Turning to the figures, FIG. 1 shows a system 100 according to one or more embodiments of the disclosed subject matter. System 100 can be comprised of a base station 200 and a handset 300, which may be referred herein as a hand-held device. Optionally, the base station 200 and the handset 300 may be connected to each other via a transmission medium 400, which may provide power from the base station 200 to the handset 300 and communications between the base station 200 and the handset 300.

The transmission medium 400 may be a plurality of wired transmission lines, for instance, separately insulated inside a single transmission cord or separate transmission cords, where one of the wired transmission lines can transmit relatively high voltage from the base station 200 to the handset 300 and another transmission line (or lines) can provide relatively low voltage, communication signals, and grounding for the handset 300. Thus, in one or more embodiments, the low voltage transmission can be implemented via a low voltage cable bundle for power and communications to the handset 300 (e.g., for a motor and/or controller of the handset 300); a ground cable may be integrated into the low voltage cable bundle or, alternatively, the ground cable may be a separate cable. Alternatively, some or all of the signals can be transmitted wirelessly between the base station 200 and the handset 300. That is, the handset 300 may be a wireless handset.

Generally, for electrospinning or electrospraying, the surface on which the fibers or droplets, respectively, are to be deposited on should or must be at or near ground potential. As such, the deposit surface, such as skin of a user, should be grounded during the electrospinning or electrospraying process. In terms of grounding a user, this may be accomplished by grounding the user to the base station 200, the handset 300, or some other structure. For example, the user may be grounded via a grounding strap 501 attached to the user and a grounding line 500 connected to the base station 200, such as shown in FIG. 1, via a grounding line 502 connected to the handset 300, via a rod or a plate on a grip of the handset 300 and optionally a grounding strap 501 attached to the user, or via a grounding route separate from the base station 200 and the handset 300, such as a grounding route integrated into a chair, seat, table, metal plate, or other structure. Also, in the case of someone other than the user (e.g., an esthetician) using the handset 300 to apply the electrospun or electrosprayed solution to the user, the other person may also be grounded, for example, via the handset 300 or a separate grounding route, such as described above.

The base station 200 can include a control panel 202 and circuitry, which may include a controller or controllers 204 and/or a power source 206. Optionally, the circuitry can include computer-readable memory (not expressly shown) configured to store settings and/or programming code executable by the controller 204, to control the power source 206, the control panel 202, and the handset 300. In one or more embodiments, the base station 200 may include a handset receptacle 208 configured to receive and physically hold or stow the handset 300. Optionally, the base station 200 may include a timer settable and viewable by the user, for instance. In one or more embodiments of the disclosed subject matter, the base station 200 may have relatively less functionality than described above. For example, the base station 200 may simply have the handset receptacle 208 and therefore act only as a holder or receptacle for the handset 300.

The control panel 202 may be configured to receive control inputs to control the handset 300 and the base station 200 by way of the controller 204, for instance. For example, the control panel 202 may have a control input to control high voltage to the handset 300, a control input to control motor direction of a motor (e.g., stepper motor) of the handset 300, and/or a control input to control flow rate of the handset 300 (e.g., speed of the motor of handset 300). The control panel 202 may also have a power on/off control input to control an on/off state of the base station 200 and, optionally, whether some or all of the voltage and communication signals are supplied to the handset 300. The user input interfaces can be knobs, switches, buttons, a touch panel or screen, or a combination some or all of the foregoing. Further, such user input interfaces may identify relatively simple predetermined settings for various operational characteristics controllable by the user via the control panel 202.

Optionally, control panel 202 may include a display (not expressly shown), such as a liquid crystal display (LCD) or Light Emitting Diode (LED) display, which may be a touch screen or panel, as noted above. The display may output information corresponding to operating characteristics of the handset 300, such as flow rate, an amount of high voltage received by the handset 300 or otherwise applied to the solution to perform electrospinning or electrospraying, a status of the handset 300, a direction of the motor of the handset, and/or whether appropriate grounding of the user is provided. Additionally or alternatively, the display may output information corresponding to operating characteristics of the base station 200, such as an amount of high voltage supplied to the handset 300, the on/off state, whether the handset 300 is detected by the base station 200 to be docked in the handset receptacle 208, and/or whether power is supplied to the base station 200 by an internal or external power source.

The power source 206 may be or include a relatively low voltage power source, such as 5 VDC supplied from an onboard power source (e.g., a battery or batteries) or an external source, such as mains (e.g., from a wall electrical receptacle), in which case the voltage would be converted from AC to the relatively low DC voltage, or an external battery unit. Of course, in the case of mains, the power source 206 can have an AC/DC converter to convert the mains to the relatively low voltage. Generally, components of the base station 200, such as the control panel 202 and the controller 204, may be supplied power from the power source 206, particularly the relatively low voltage.

Optionally, the power source 206 may be or include a relatively high voltage power source to provide a corresponding high voltage to the handset 300. The power source 206 may have or be coupled to a transformer that converts a relatively low voltage, such as the above-referenced 5 VDC, to the relatively high voltage, particularly a relatively high DC voltage. The high voltage should be sufficiently high to create an electric field that can generate a Taylor cone of the solution; also a current supply sufficient to charge up the solution and also overcome parasitic losses/capacitances should be supplied. Thus, in embodiments of the disclosed subject matter, the power source 206 can high voltage with sufficient current output to perform a desired electrospin or electrospray operation. The high DC voltage may be preferably about 15 kV DC; more preferably about 7 kV DC to about 30 kV DC; and most preferably about 8 kV DC to about 20 kV DC. Optionally, the high voltage may be controllable using the control panel 202, for instance, preferably from about 7 kV DC to about 30 kV DC; more preferably about 8 kV DC to about 20 kV DC.

The relatively high voltage HV can be supplied to the handset 300 via the transmission medium 400, under control of the control panel 202 and controller 204, for instance. Further, the relatively high voltage can be provided to the handset 300 to generate an electric field (EF) in and around a solution contained in the handset 300 to output the solution in electrospun or electrospray format. Alternatively, the high voltage power source may be provided in the handset 300.

Incidentally, the transmission medium 400 (or portions thereof) may be removably coupled to the base station 200. Thus, different handsets, such as handset 300, may be coupled to the same base station 200. The control panel 200 may be used to control settings, configurations, etc. based on the particular handset coupled to the base station 200. Optionally, the base station 200 may detect the type of handset and automatically set some or all settings, configurations, etc. based on the detected type. Alternatively, the base station 200, via the control panel 202, may display options so the user may set the settings, configurations, etc. based on the particularly type of handset. Likewise, the grounding line 500 may be removably coupled to the base station 200.

Alternatively, the system 100 may be comprised of the handset 300 and not the base station 200. That is, in one or more embodiments, components of the base station 200 may be implemented in the handset 300 such that the handset 300 can be fully operational as a stand-alone electrospinning or electrospraying apparatus. For example, the handset 300 can have a power source to provide a high voltage HV to perform the electrospinning or electrospraying process and a power source to provide relatively low voltage (e.g., 5 VDC) to power other components of the handset 300, such as an electric motor of the handset 300. Optionally, the transmission medium 400 may still be coupled to the handset 300, for instance, to provide power from mains (e.g., a wall receptacle). Of course, in the latter case the transmission medium 400 may not need to accommodate relatively high voltage, since such high voltage is now provided by the handset 300. Alternatively, the handset 300 may be powered locally, using a battery or batteries, capacitors, etc. directly coupled to or in the handset 300.

The handset 300 can be comprised of a body assembly 310 and an output assembly 330, which may be referred to herein as a durable portion and a semi-durable portion, respectively. The output assembly 330 can be removably coupled to the body assembly 310, for instance, using a snap-fit connection or connections. The output assembly 330 can have an outlet or nozzle 334 or, alternatively, be coupled to the nozzle 334. Thus, in one or more embodiments, the nozzle 334 can be removably coupled to the output assembly 330. Generally, the user can provide a control input to the body assembly 310 to cause a high voltage HV and thus a corresponding electric field to be applied in and around solution in the output assembly 330, such that the solution is output in electrospun or electrospray-fashion from the nozzle 334.

The body assembly 310 may be deemed a durable portion in that the body 310 assembly may be used over and over again. Of course, the body assembly 310 may itself have consumables, such as a battery or batteries. The output assembly 330 may be deemed a semi-consumable portion configured to removably hold a consumable portion, because some of the output assembly 330 can be reused and some of the output assembly 330 can be replaced. For example, the semi-consumable portion may have a consumable portion housing that is removable from the semi-durable portion and replaceable with a different (e.g., larger) consumable portion housing configured to receive and hold a different (e.g., larger) consumable portion. The consumable portion can be replaced in the corresponding consumable portion housing.

The output assembly 330 can contain the solution, for instance, in a consumable portion. The consumable portion can be comprised of a container (e.g., carpule, cartridge, etc.) configured to hold and output the solution. When the consumable portion is empty or if another type of solution is desired, the output assembly 330 may be removed from the body assembly 310 and the consumable portion presently in the output assembly 330 may be removed and replaced with another consumable portion of a same configuration. Alternatively, as noted above, a consumable portion housing (and the consumable portion held therein) may be removed from the output assembly 330 and replaced with another consumable portion housing having a different configuration. Another consumable portion with a configuration matching the configuration of the consumable portion housing may be inserted into the different consumable portion housing.

Figure 2A:
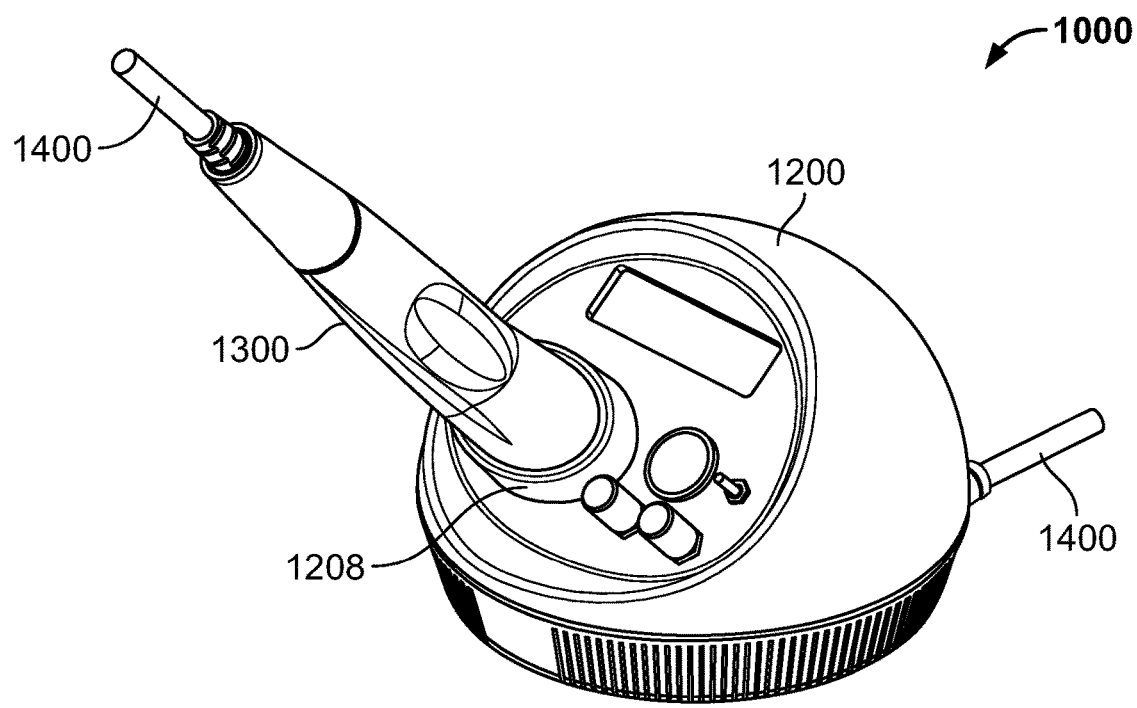
Figure 2B:
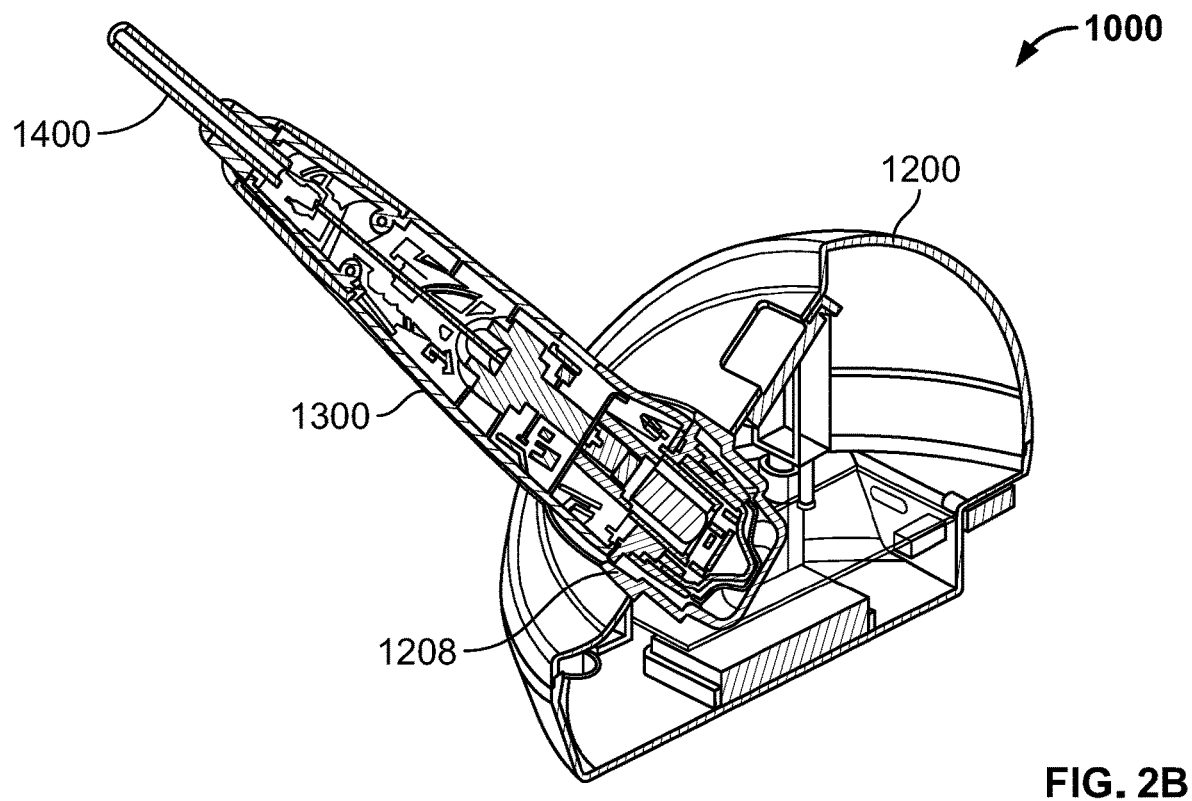

FIGS. 2A and 2B show a system 1000 according to one or more embodiments of the disclosed subject matter. The system 1000 can be comprised of a base station 1200 and a hand-held device 1300. A transmission medium 1400 can connect the base station 1200 to the hand-held device 1300 (not expressly shown). Of course, in one or more embodiments the transmission medium 1400 may be a wireless transmission medium exclusively, or a combination of wire and wireless transmission media. As shown, the base station 1200 can have a hand-held device receptacle 1208 configured to receive and physically hold or stow the hand-held device 1300.

Turning to FIGS. 3A-3F, operation of the base station 1200 can be as described above for the base station 200. The base station 1200 may be coupled to a separate power supply (e.g., mains) via a power cable (not expressly shown), which may be fixed to or detachable from the base station 1200. The base station 1200 shows a non-limiting example of a control panel 1202 according to one or more embodiments of the disclosed subject matter.

The control panel 1202 may be configured to receive control inputs 1212 to control the hand-held device 1300 and the base station 1200 by way of a controller (not expressly shown), for instance. For example, the control panel 1202 may have as control inputs 1212 a control input to control high voltage to the hand-held device 1300, a control input to control motor direction of a motor (e.g., stepper motor) of the hand-held device 1300, and/or a control input to control flow rate of the hand-held device 1300 (e.g., speed of the motor of hand-held device 1300). The control panel 1202 may also have as one of the control inputs 1212 a power on/off control input to control an on/off state of the base station 1200 and, optionally, whether some or all of the voltage and communication signals are supplied to the hand-held device 1300. The control inputs 1212 can be user input interfaces in the form of knobs, switches, buttons, a touch panel or screen, or a combination some or all of the foregoing. Further, such user input interfaces may identify relatively simple predetermined settings for various operational characteristics controllable by the user via the control panel 1202.

The control panel 1202 can include a display 1210, such as a liquid crystal display (LCD) or Light Emitting Diode (LED) display, which may be a touch screen or panel. The display 1210 may output information corresponding to operating characteristics of the held device 1300, such as flow rate, an amount of high voltage received by the held device 1300 or otherwise applied to the solution to perform electrospinning or electrospraying, a status of the held device 1300, a direction of the motor of the handset, and/or whether appropriate grounding of the user is provided. Additionally or alternatively, the display 1210 may output information corresponding to operating characteristics of the base station 1200, such as an amount of high voltage supplied to the hand-held device 1300, the on/off state, whether the hand-held device 1300 is detected by the base station 1200 to be docked in the hand-held device receptacle 1208, and/or whether power is supplied to the base station 1200 by an internal or external power source.

The base station 1200 can also include circuitry, which may include a controller or controllers and/or a power source (not expressly shown). Optionally, the circuitry can include computer-readable memory (not expressly shown) configured to store settings and/or programming code executable by the controller, to control the power source, the control panel 1202, and the hand-held device 1300. Optionally, the base station 1200 may include a timer settable and viewable by the user, for instance (not expressly shown).

FIGS. 4A-4F show various views of the hand-held device 1300, according to various embodiments of the disclosed subject matter.

The hand-held device 1300 can be configured to electrospin or electrospray a predetermined solution toward a deposit surface. The hand-held device 1300 can be comprised of a durable portion 1310, a semi-durable portion 1330, and a consumable portion 1350 (not shown in FIGS. 4A-4F). In one or more embodiments, the hand-held device 1300 may be interpreted as consisting of the durable portion 1310, the semi-durable portion 1330, and the consumable portion 1350. Discussed in more detail below, the semi-durable portion 1330 can be removably coupled to the durable portion 1310, and the consumable portion 1350 can be removably coupled to the semi-durable portion 1330.

An optional cap 1305 can be provided, which may be removably coupled (e.g., via a snap fit connection or a threaded connection) to the semi-durable portion 1330. Alternatively, the cap 1305 may be removably coupled to the semi-durable portion 1330 and an end of the durable portion 1310, such as to a collar 1312. As yet another alternative, the cap 1305 may be removably coupled to only the end of the durable portion 1310, such as the collar 1312. In one or more embodiments, the cap 1305 may be considered part of the semi-durable portion 1330. The durable portion 1310 may be coupled to the transmission medium 1400, which, in turn, may be coupled to a base station, such as the base station 1200.

Figure 4A:
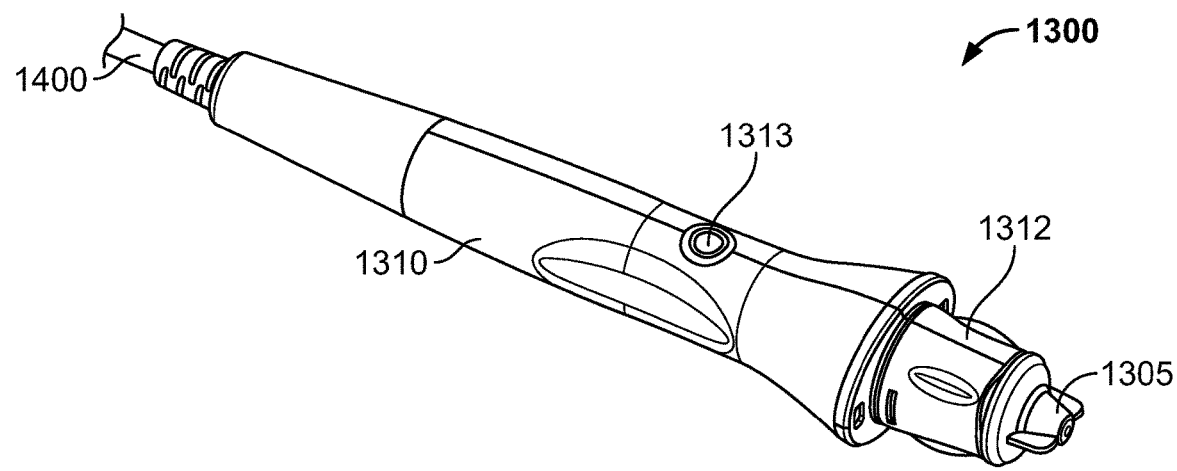
Figure 4B:
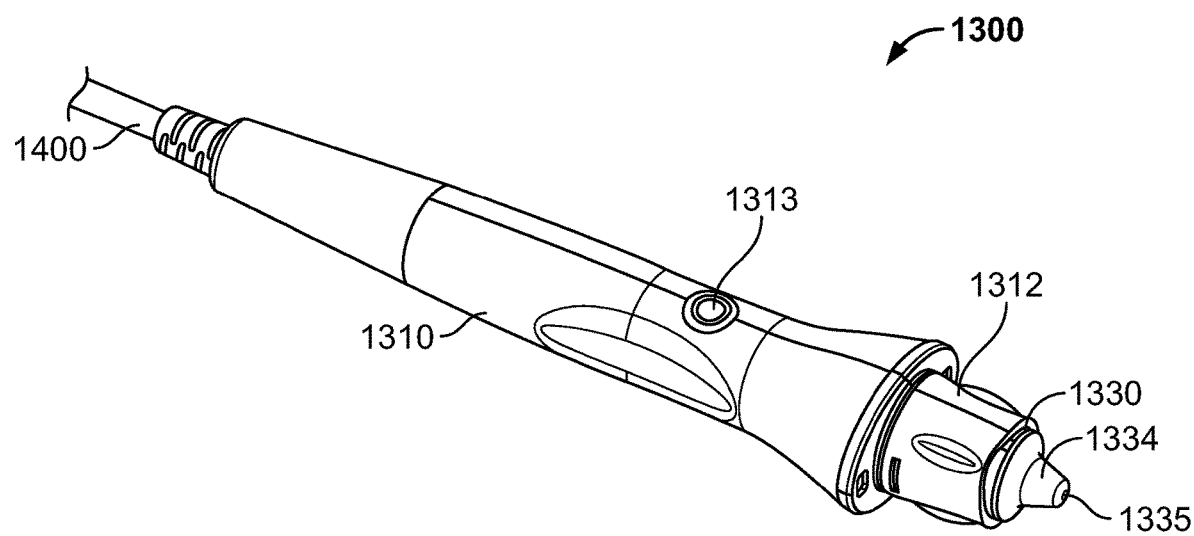
Figure 4C:
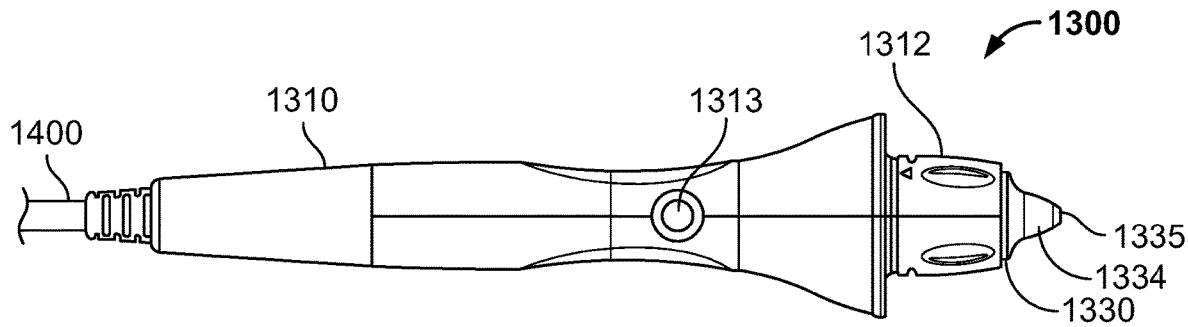
Figure 4D:
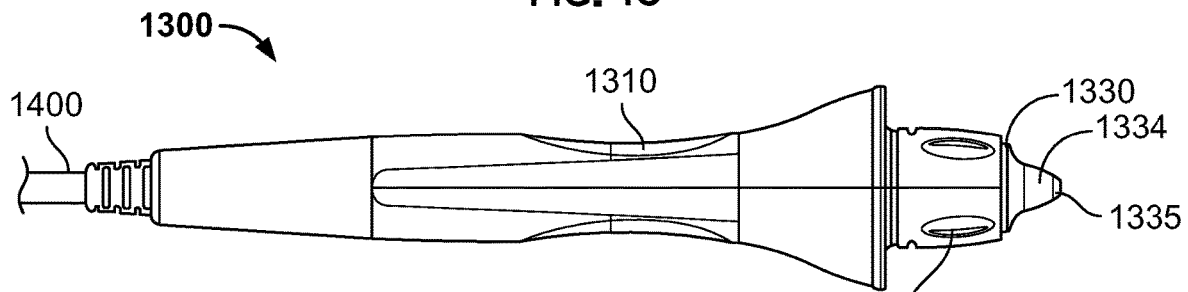
Figure 4E:
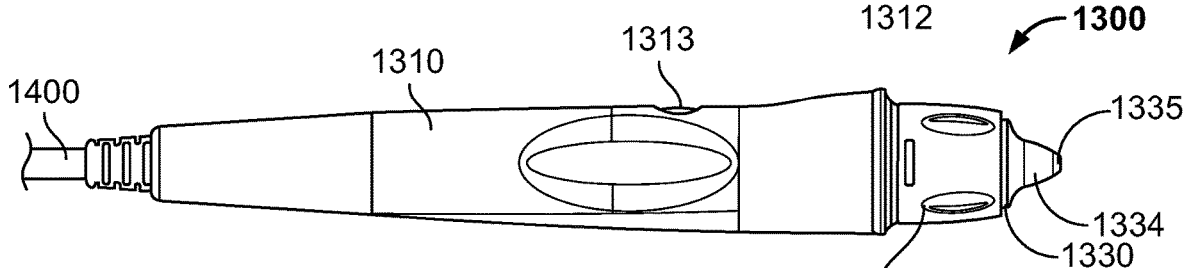
Figure 4F:
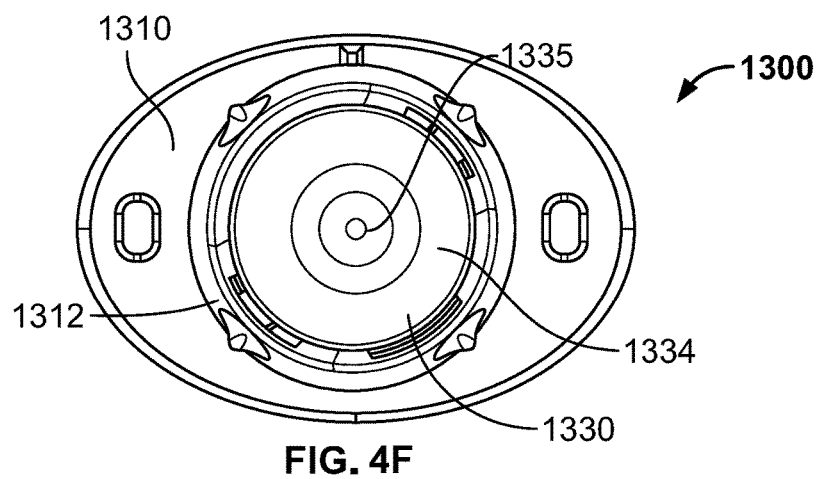
Figure 4G:
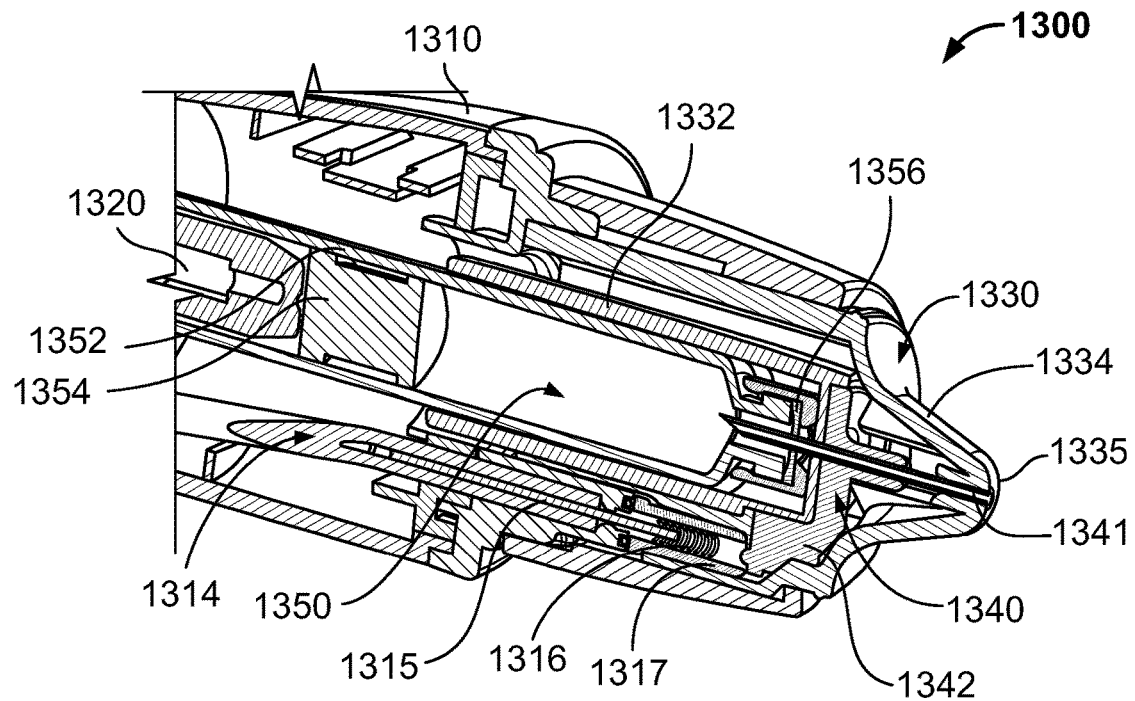
Figure 4H:
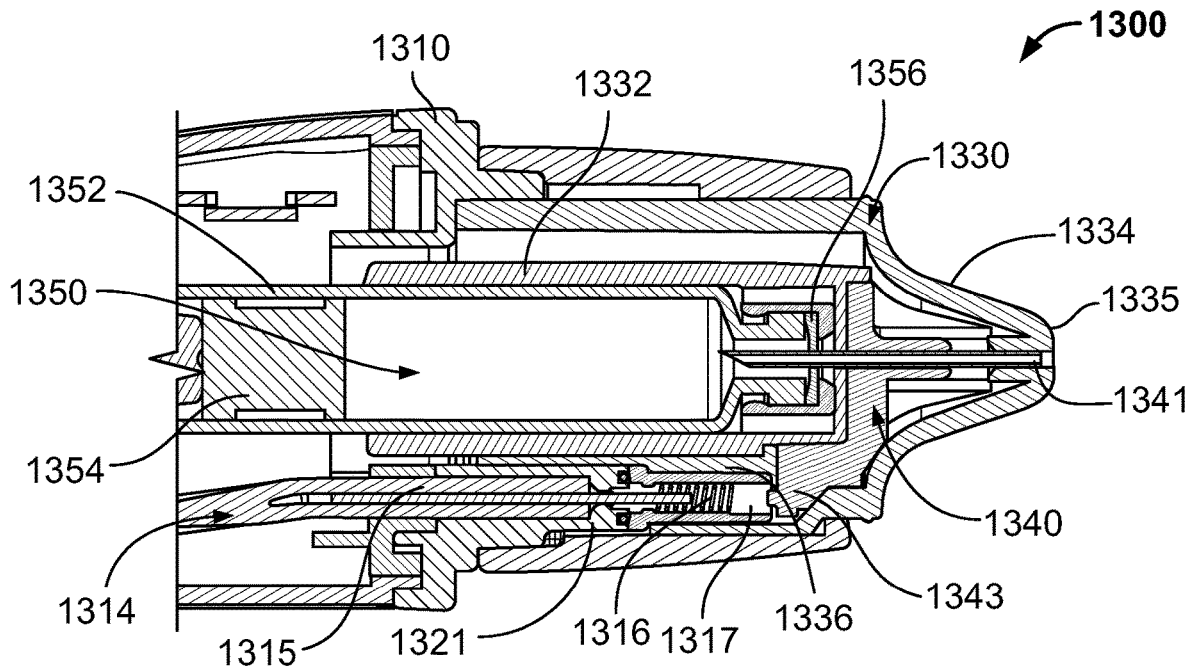

FIGS. 4G-4H are enlarged perspective sectional views of an end portion of the hand-held device 1300. Notably, these figures show the consumable portion 1350 inside the semi-durable portion 1330 and the durable portion 1310 when the semi-durable portion 1330 is removably coupled to the durable portion 1310. When the semi-durable portion 1330 is removably coupled to the durable portion 1310, an outer peripheral surface of the semi-durable portion 1330 may be exposed to the outside. That is, the durable portion 1310 may not cover a portion of the outer peripheral surface of the semi-durable portion 1330 when the semi-durable portion 1330 is connected to the durable portion 1310.

In one or more embodiments of the disclosed subject matter, the consumable portion 1350 may have an end that extends from the semi-durable portion 1330, into the durable portion 1310. A portion of the consumable portion 1350 inside the semi-durable portion 1330 may be more than a portion that is inside only the durable portion 1310. For example, the semi-durable portion 1330 may have a consumable portion housing 1332 configured to hold the consumable portion 1350, where a length of the consumable portion 1350 associated with an end portion thereof that is held by the consumable portion housing 1332 can be greater than a length of the consumable portion 1350 associated with an opposite end portion thereof that extends from the semi-durable portion 1330. Alternatively, a portion of the consumable portion 1350 inside the semi-durable portion 1330 may be less than a portion that is inside only the durable portion 1310. For example, a length of the consumable portion 1350 associated with an end portion thereof that is held by the consumable portion housing 1332 can be less than a length of the consumable portion 1350 associated with an opposite end portion thereof that extends from the semi-durable portion 1330. The amount of the consumable portion 1350 that extends from the consumable portion housing 1332, for instance, can be based on desired holding characteristics for the consumable portion 1350 and/or a means by which the consumable portion 1350 is to be pulled out of the consumable portion housing 1332 (e.g., via a user's fingers or a specialized removal tool). Further, in some embodiments, the consumable portion housing 1332 may form an extremity of the semi-durable portion 1330.

FIGS. 5A-5G show various views of the durable portion 1310 of the hand-held device 1300 according to one or more embodiments of the disclosed subject matter. The durable portion 1310 can be configured to be held by the user during an electrospraying or electrospinning operation. Generally, with reference to FIGS. 4G, 4H, and 5A-5G, the durable portion 1310 can include a body with a user control interface 1313 configured to receive manual input from the user to control a drive mechanism 1318 and application of high voltage, via a high voltage line 1314, to an electrode 1340 of the semi-durable portion 1330 to create an electric field for application to the solution to electrospin or electrospray the solution from a nozzle 1334 of the semi-durable portion 1330 toward a deposit surface. Incidentally, embodiments of the disclosed subject matter can have a single electrode or multiple electrodes or electrode portions.

In addition to the user control interface 1313, the durable portion 1310 can have the drive mechanism 1318, which can be configured to cause the solution within a container 1352 of the consumable portion 1350 to be output to the electrode 1340 of the semi-durable portion 1330. The drive mechanism 1318 can include a motor 1319 and an actuator 1320. The motor 1319 of the drive mechanism 1318 may be a stepper motor, for instance, that drives the actuator 1320, which may be a linear actuator. The motor 1319 and actuator 1320 can be controlled based on operation of the user control interface 1313. Generally speaking, actuation of the actuator 1320, which may be in response to activation of the user control interface 1313, can drive a boss thereof against a plunger 1354 relative to the container 1352 of the consumable portion 1350 (described in more detail below) to cause the plunger 1345 to move inside the container 1352 and cause solution in the container 1352 to be output from the container 1352 to the nozzle 1334 for application of high voltage and output from the nozzle tip 1335 as electrospun or electrosprayed solution.

Optionally, the motor 1319 may be programmable, for instance, using circuitry (not expressly shown) of the durable portion 1310. Such programming may provide for different flow profiles to be used based on particular application conditions, such as environment, type of solution to be applied, high voltage applied, etc. Optionally, the actuator 1320 can be controlled, prior to an electrospinning or electrospraying operation, to prime the hand-held device 1300 by removing air from the solution flow path. Additionally, the motor 1319 and the actuator 1320 may not provide back suction. That is, in one or more embodiments, back suction of the solution may not be provided. Alternatively, the motor 1319 and the actuator 1320 may be controlled to provide back suction, for instance, for a predetermined duration of time. The predetermined duration of time may be preferably about 0.1 seconds; more preferably about 0.5 seconds, after stopping output of the solution from the nozzle 1334.

Circuitry (not expressly shown) of the durable portion 1310 may be comprised of a power supply, which may provide low and high voltage to respective components of the hand-held device 1300. For example, the power supply can provide high voltage to the high voltage line 1314. Optionally, at least a portion of the circuitry may be implemented via a printed circuit board (PCB). In one or more embodiments, the high voltage high voltage line 1314 may be considered part of the circuitry.

Figure 11:
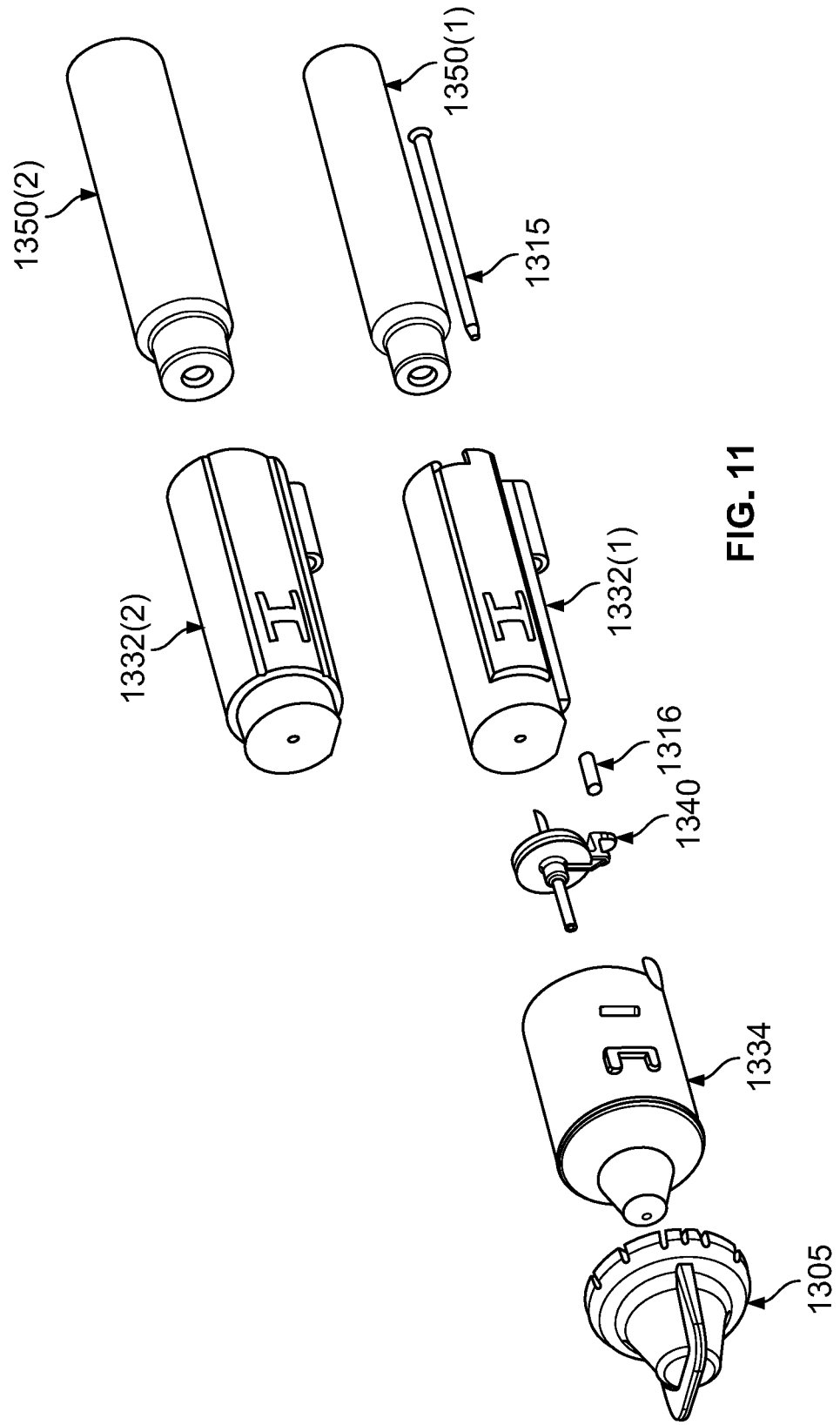

As shown in FIGS. 4G and 4H, the high voltage line 1314 can extend toward and be electrically connected to the electrode 1340 of the semi-durable portion 1330 when the semi-durable portion is connected to the durable portion 1310. A conductive rod 1315, an electrode spring 1316, and a contact 1317 may be provided as an electrical connection for the high voltage line 1314 and the electrode 1340 of the semi-durable portion 1330. In one or more embodiments, the conductive rod 1315, the electrode spring 1316, and the contact 1317 may be considered part of the high voltage line 1314. In an alternative embodiment, such as shown in FIG. 11, the conductive rod 1315 and the electrode spring 1316 may be provided without the contact 1317, and such conductive rod 1315 and electrode spring 1316 may be considered part of the semi-durable portion 1330. Of course, the conductive rod 1315 can contact an electrical contact (not shown in FIG. 11) of the durable portion 130 at a far end of the conductive rod 1315.

The electrical connection formed by at least the conductive rod 1315 and the electrode spring 1316 may be deemed a spring-loaded pogo connector, which may be operative to have the high voltage supplied therethrough only when the semi-durable portion 1330 is properly coupled to the durable portion 1310. That is, the electrode 1340 of the semi-durable portion 1330 may receive high voltage from the high voltage line 1314 when the semi-durable portion 1330 is properly connected to the durable portion 1310, because the circuit formed by these components is completed and capable of receiving and providing the high voltage. Discussed in more detail below with reference to FIGS. 12A-12C, the semi-durable portion 1330 may be slid into the durable portion 1310 and, as such, the electrical connection can be considered a slide-in electrical connection. Such slide-in electrical connection can increase a distance at which an arc would have to travel.

The high voltage line 1314 (or a portion thereof), the conductive rod 1315, the electrode spring 1316, and/or the contact 1317 can be surrounded by insulation. Such insulation can be insulation of the semi-durable portion 1330 and/or insulation of the durable portion 1310, depending upon the location of the power-related component. Optionally, the insulation can be part of a housing of the semi-durable portion 1330 and/or a housing of the durable portion 1310. Additionally or alternatively, the insulation can be a separate insulation component or components inside the housing of the semi-durable portion 1330 and/or the housing of the durable portion 1310. Further, such insulation can be in the form of non-conductive plastic. In one or more embodiments of the disclosed subject matter, a portion of the high voltage line 1314, the conductive rod 1315, the electrode spring 1316, and the contact 1317 may be positioned at, on, or outside an outer circumference of the consumable portion housing 1332.

Figure 5A:
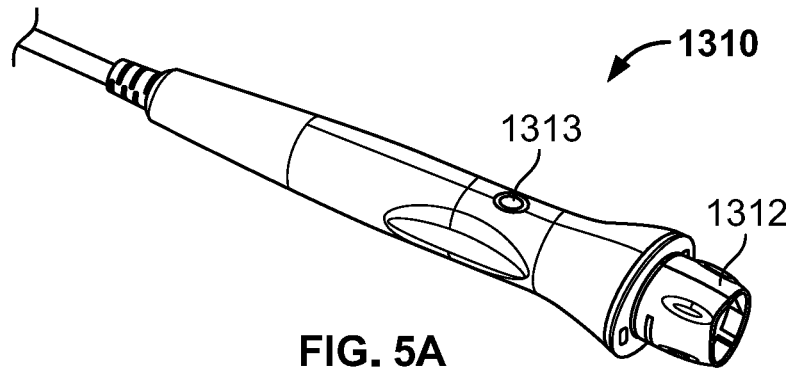
Figure 5B:
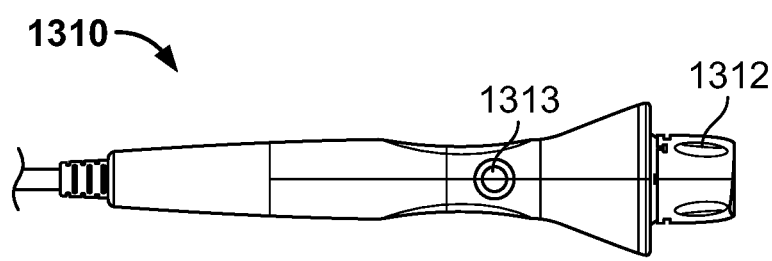
Figure 5C:
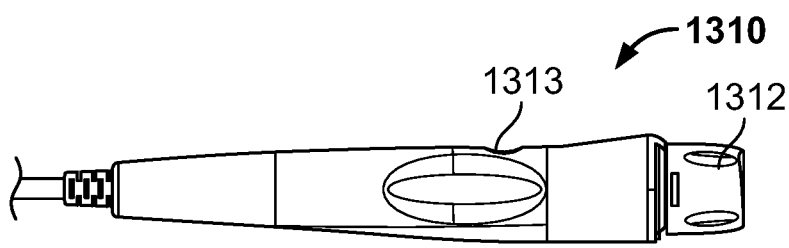
Figure 5D:
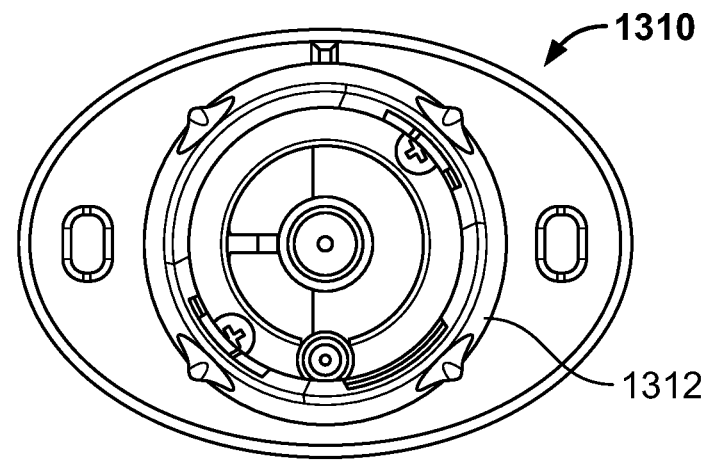
Figure 5G:
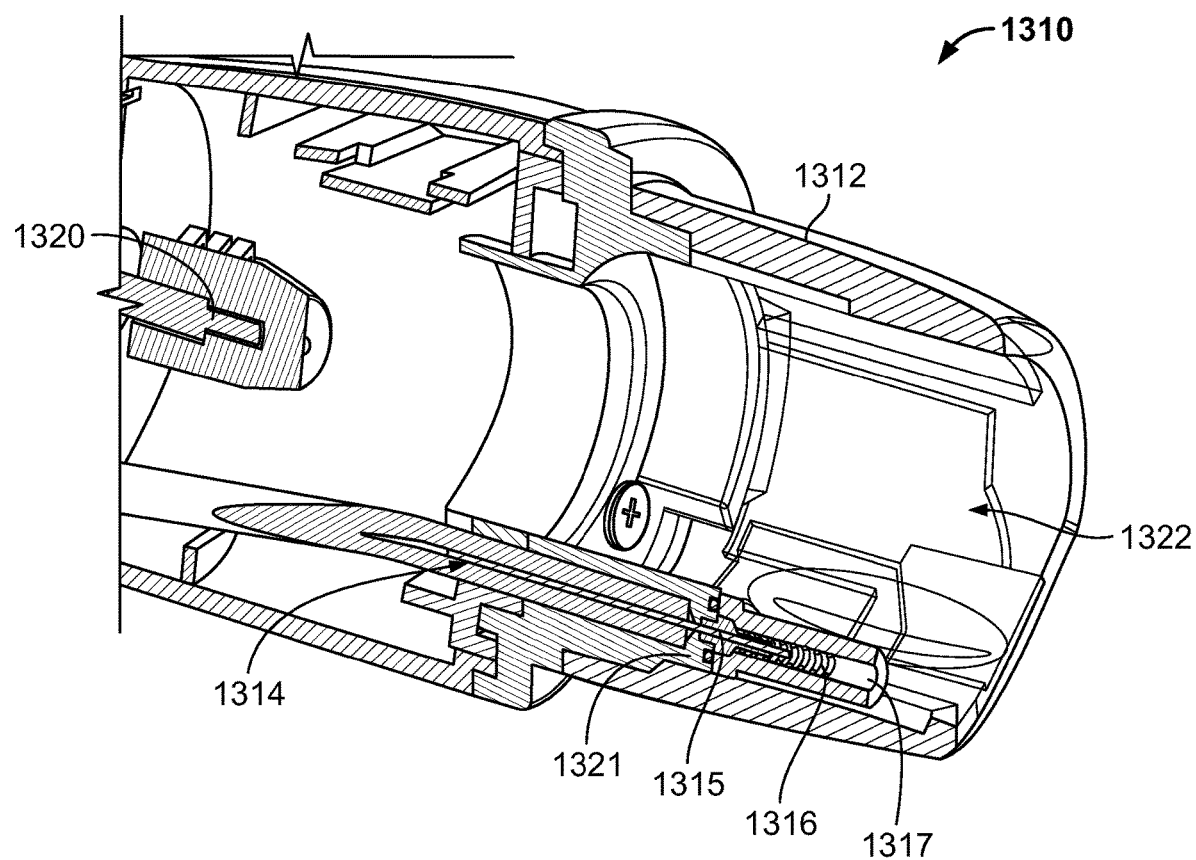
Figure 12A:
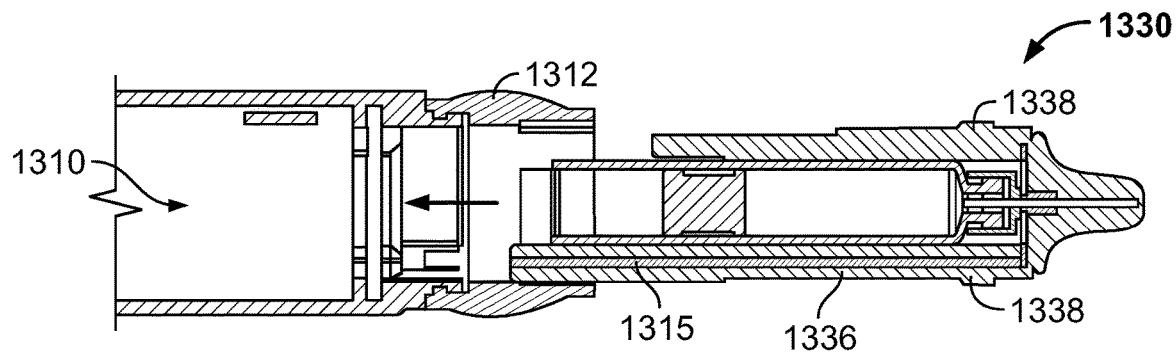
FIGS. 12A-12C illustrate insertion and locking aspects of a semi-durable portion and a durable portion according to one or more embodiments of the disclosed subject matter.
Figure 12B:
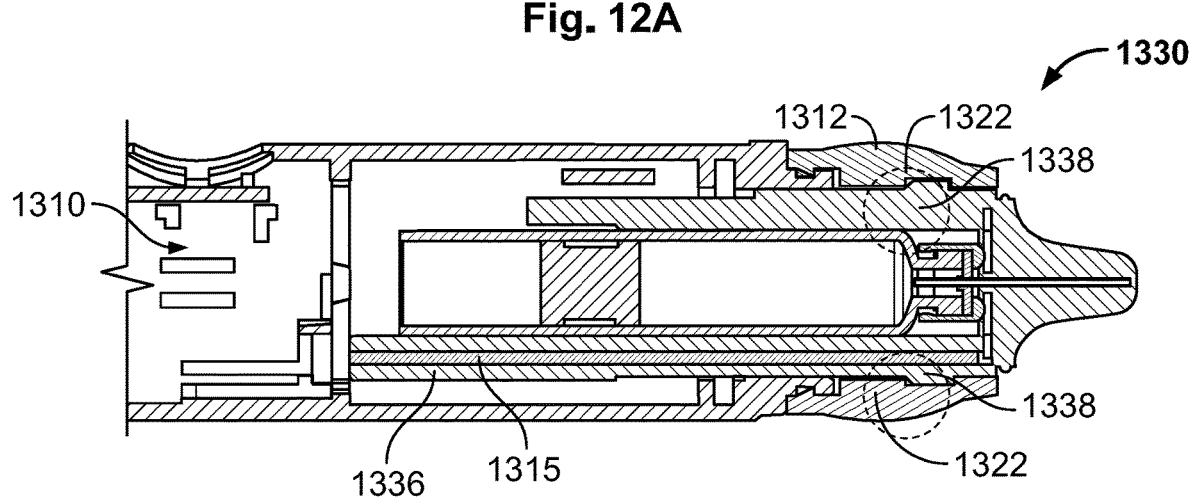

For example, FIGS. 4G, 4H, and 5G show an insulating portion (or portions) 1321 of the durable portion 1310 which surrounds a portion of the high voltage line 1314 (including the conductive rod 1315), and FIGS. 4G and 4H show an insulating portion (or portions) 1336 of the semi-durable portion 1330, which surrounds a portion of the high voltage line 1314 (including the conductive rod 1315, the electrode spring 1316, and the contact 1317). As another example, FIGS. 12A and 12B show an embodiment where an insulating portion (or portions) 1336 surrounds the conductive rod 1315. The insulating portion 1336 of FIGS. 12A and 12B may be in the configuration of an insulating rod.

The user control interface 1313 can include or be in the form of switch, for instance, a trigger button or a toggle switch. Optionally, the trigger button or switch can be connected to ground. The user control interface 1313 can be activated by user input, for instance, a user's finger or thumb, to activate the hand-held device 1300. Specifically, the user control interface 1313 can be activated by the user to activate the motor 1319 to control the actuator 1320 to cause solution in the container 1352 to be output to the nozzle 1334 and output from the nozzle tip 1335, to activate providing the high voltage to the electrode 1340 to create a corresponding electric field for application to the solution, or both.

The user control interface 1313, for instance, the switch, can be provided at a predetermined distance or spacing from the high voltage line 1314. For example, as shown in FIGS. 5E and 5F, the switch may be at a first side of the durable portion 1310 and the high voltage line 1314 may be at a second side of the durable portion 1310 opposite the first side in a radial direction. Put another way, the switch may be 180 degrees offset from the high voltage line 1314 in a tangential direction. Of course, embodiments of the disclosed subject matter can embody different offset amounts. For example, in one or more embodiments of the disclosed subject matter, the switch may be offset from the high voltage line 1314 by about 60 degrees to about 300 degrees, preferably about 180 degrees, in the tangential direction. Optionally, the durable portion 1310 may have at least one attachment arrangement configured to detachably hold an accessory (not expressly shown).

Optionally, the user control interface 1313 may be a multi-stage user interface, such as a half/full press tactile switch. Thus, for example, the first stage may be to check the settings of the hand-held device 1300, for instance, to identify whether the hand-held device 1300 is suitably positioned—i.e., not too far away and/or not too close— relative to the deposit surface (e.g., skin of the user). That is, the first stage may be used to for depth adjustment of hand-held device 1300 before outputting the electrospun or electrosprayed solution. The second stage may be to cause output of the electrospun or electrosprayed solution by controlling the motor 1319 and the high voltage applied to and around the solution.

Optionally, the durable portion 1310, for instance, the circuitry thereof, can include at least one distance sensor (not expressly shown). For example, each at least one distance sensor can be a time of flight (TOF) sensor. In one or more embodiments, the distance sensor may be deemed a separate component or components from the circuitry. The one or more distance sensors according to one or more embodiments of the disclosed subject matter may be offset in the tangential direction from the high voltage line 1314.

For example, each at least one distance can be offset from about 60 degrees to about 300 degrees, preferably about 180 degrees, from the high voltage line 1314.

Generally, the distance sensor can determine distance of the hand-held device 1300, for instance, the nozzle tip 1335, from a deposit surface. Signals from the distance sensor can be provided to control operations of the hand-held device 1300. For example, signals from the distance sensor can be provided to the circuitry to control, for instance, disable, the motor 1319 and/or the user control interface 1313. That is, optionally, based on signals from the distance sensor, the hand-held device 1300 can be automatically shut off the high voltage supply to the electrode 1340. Such control may be performed when signals from the distance sensor indicate that the hand-held device 1300 is positioned too far away from and/or too close to the deposit surface. The signals from the distance sensor can also be processed by the circuitry to identify whether the hand-held device 1300 is suitably positioned relative to the deposit surface and therefore allow operation of the hand-held device 1300 to output electrospun or electrosprayed solution to the deposit surface.

Generally, too far away may be defined as greater than about 150 mm, preferably about 120 mm or greater. For example, about 120 mm to about 150 mm may be deemed too far away, and greater than 150 mm may be deemed unacceptably too far away, for instance, where substandard or defective electrospraying or electrospinning can occur. Generally, too close may be defined as closer than about 30 mm, preferably about 50 mm or closer. For example, about 30 mm to about 50 mm may be deemed too close, and closer than about 30 mm may be deemed unacceptably too close, for instance, in terms of the high voltage relative to the deposit surface. Thus, an acceptable threshold may be from about 30 mm to about 50 mm to about 100 mm to about 120 mm, preferably about 50 mm to about 100 mm, for instance.

The circuitry may be comprised of a solution fill level detector (not expressly shown) configured to detect an amount of solution in the consumable portion 1350. Alternatively, the solution fill level detector may be deemed a separate component or components from the circuitry. The solution fill level detector may include or may be implemented using a Hall effect sensor array. The solution fill level detector may send signals regarding an amount or fill level of solution in the container 1352 to a processor of the circuitry, which may send the signals to the base station 1200. Alternatively, the signals can be sent directly from the solution fill level detector to the base station 1200. As yet another alternative, the signals may be processed by the processor and not sent to a base station (e.g., when a base station is not implemented).

A detector may be provided to detect proper connection of the semi-durable portion 1330 to the durable portion 1310. Additionally, the detector may detect proper connection of the consumable. Such detector may be provided in the durable portion 1310. For example, when the semi-durable portion 1330 is properly connected to the durable portion 1310, the detector may output a signal or signals to indicate that the semi-durable portion 1330 is coupled to the durable portion 1310. Optionally, such signal(s) may control a feedback indicator on the durable portion 1310 to output an indication of such proper coupling. Additionally or alternatively, such signal(s) may allow activation of the user control interface 1313 and/or the high voltage to the electrode 1340. Conversely, absence of the signal(s) may cause deactivation of the user control interface 1313 and/or the high voltage to the electrode 1340. Thus, proper connection can mean that power from the high voltage line 1314 can be provided to the electrode 1340 and that such connection can perform electrospinning or electrospraying of solution from the consumable portion 1350 from the nozzle tip 1335. In one or more embodiments, the detector may be a detection switch in the form of a lever switch, whereby the semi-durable portion 1330 can activate the switch when properly inserted into the durable portion 1310. Alternatively, the detection switch may be in the form of a push switch, whereby the semi-durable portion 1330 can activate the switch when properly inserted into the durable portion 1310.

Additionally or alternatively, the durable portion 1310 may have a detector configured to detect when the consumable portion 1350 is removably coupled to the semi-durable portion 1330 when the semi-durable portion 1330 is removably coupled to the durable portion 1310. Such detector may be in the form of a push or lever switch, whereby the consumable portion 1350 can activate the switch when the consumable portion 1350 is inserted in the consumable portion housing 1332, when the consumable portion housing 1332 is inserted in the nozzle 1334, and when the semi-durable is properly inserted in the durable portion 1310. Thus, the hand-held device 1300 can determine whether or not the consumable portion 1350 is provided in the semi-durable portion 1330 when the semi-durable portion 1330 is properly connected to the durable portion 1310.

Optionally, the hand-held device 1300 can have a collar 1312, which may be considered part of the durable portion 1310. Though not expressly shown in the figures, the color of the collar 1312 may be a dark, relatively less reflective color, black, for instance, to prevent or minimize unwanted feedback to a distance sensor, such as a TOF sensor, when implemented. The collar 1312 can be rotatable by a predetermined amount about an end of the body of the durable portion 1310 to lock or unlock the collar 1312 to the semi-durable portion 1330, particularly the nozzle 1334. To insert and remove the semi-consumable portion 1330 from the durable portion 1312, the collar 1312 can be rotated by a predetermined amount, for instance, about 10 to about 60 degrees, preferably about 45 degrees, to an open or unlocked position (if it was not already in this position). To lock the durable portion 1310 to the semi-durable portion 1330, the collar 1312 may be rotated in the opposite direction by a predetermined amount, for instance, about 10 to about 60 degrees, preferably about 45 degrees (if it was not already in this position). In one or more embodiments, the collar 1312 may be biased, for example, spring-loaded, to a normally closed position. Thus, to insert and remove the semi-consumable portion 1330 from the durable portion 1312, the collar 1312 may have to be rotated to an open or unlocked position. Further, the collar 1312 may have one or more undercuts, preferably at least two undercuts or fittings 1322. Such undercuts 1322 may be configured to lock the collar 1312 to the semi-durable portion 1330 when the semi-durable portion 1330 is inserted into an open end of the durable portion 1310. Further, such undercuts can engage with corresponding undercuts or fittings 1338 of the nozzle 1334. In one or more embodiments of the disclosed subject matter, the undercuts 1322 of the collar 1312 can be located at different axes as compared to the high voltage line 1314.

FIGS. 6A-6C show various views of the semi-durable portion 1330 removably connected to the consumable portion 1350 according to one or more embodiments of the disclosed subject matter. Put another way, the semi-durable portion 1330 can hold the consumable portion 1350. Notably, the consumable portion housing 1332 is inside the nozzle 1334. Optionally, as shown, a portion of the consumable portion housing 1332 may extend from an end of the nozzle 1334. These figures also show the consumable portion 1350 being inside the consumable portion housing 1332 (and the nozzle 1334). That is, the consumable portion housing 1332 can be configured to hold the consumable portion 1350. Optionally, as shown, a portion of the consumable portion 1350 may extend from the consumable portion housing 1332 (and the nozzle 1334). In one or more embodiments of the disclosed subject matter, a length of the consumable portion 1350 inside the consumable portion housing 1332 can be greater than a length of the consumable portion 1350 that extends from the consumable portion housing 1332. Alternatively, the length of the consumable portion 1350 inside the consumable portion housing 1332 can be less than a length of the consumable portion 1350 that extends from the consumable portion housing 1332.

FIGS. 6A-6C also show that one end of a tube 1341 of the electrode 1340, which may be hollow in whole or in part, can extend into the container 1352 of the consumable portion when the consumable portion 1350 is received by the semi-durable portion 1330. Further, the one end of the tube 1341 can be pointed or sharp or otherwise configured to piece a closure 1356 of the container 1352, such as shown in FIG. 6B, when extending into an inner volume of the container 1352. Such a configuration can be to facilitate providing solution from the container 1352 to the tube 1341. The tube 1341 may be made of a conductive material, such as a conductive metal.

Figure 7A:
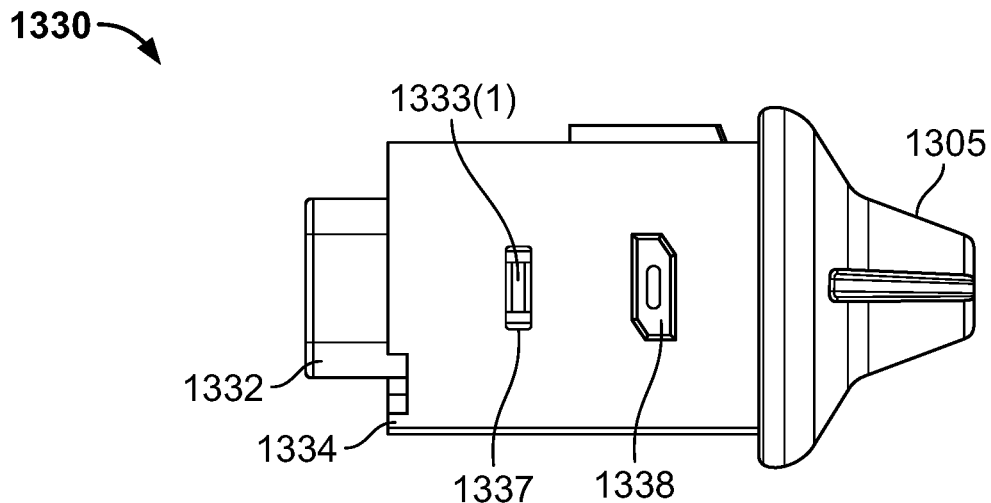
Figure 7B:
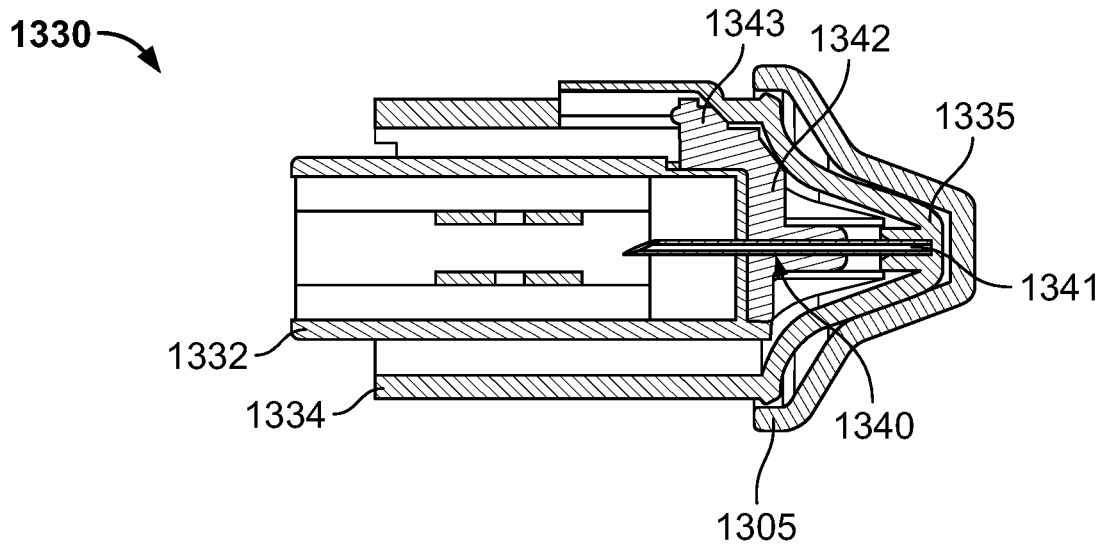
Figure 7C:
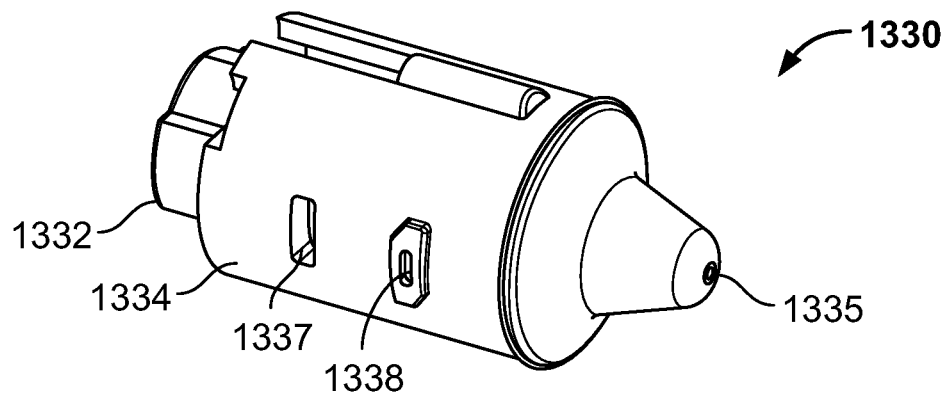

FIGS. 7A-7C show various views of the semi-durable portion 1330 without the consumable portion 1350. As noted above, the cap 1305 can be optional and may even be considered part of the durable portion 1310. Generally, the semi-durable portion 1330 can be configured to provide high voltage from the high voltage line 1314 to the electrode 1340. The high voltage of the electrode 1340 can be applied to create an electric field that is applied to solution as the solution from the consumable portion 1350 travels through the tube 1341 of the electrode 1340 and toward the nozzle tip 1335 of the nozzle 1334 and output from the nozzle tip 1335. Though not expressly shown in the figures, the color of the collar nozzle 1334 may be a dark, relatively less reflective color, black, for instance, to prevent or minimize unwanted feedback to a distance sensor, such as a TOF sensor, when implemented.

Figure 10:
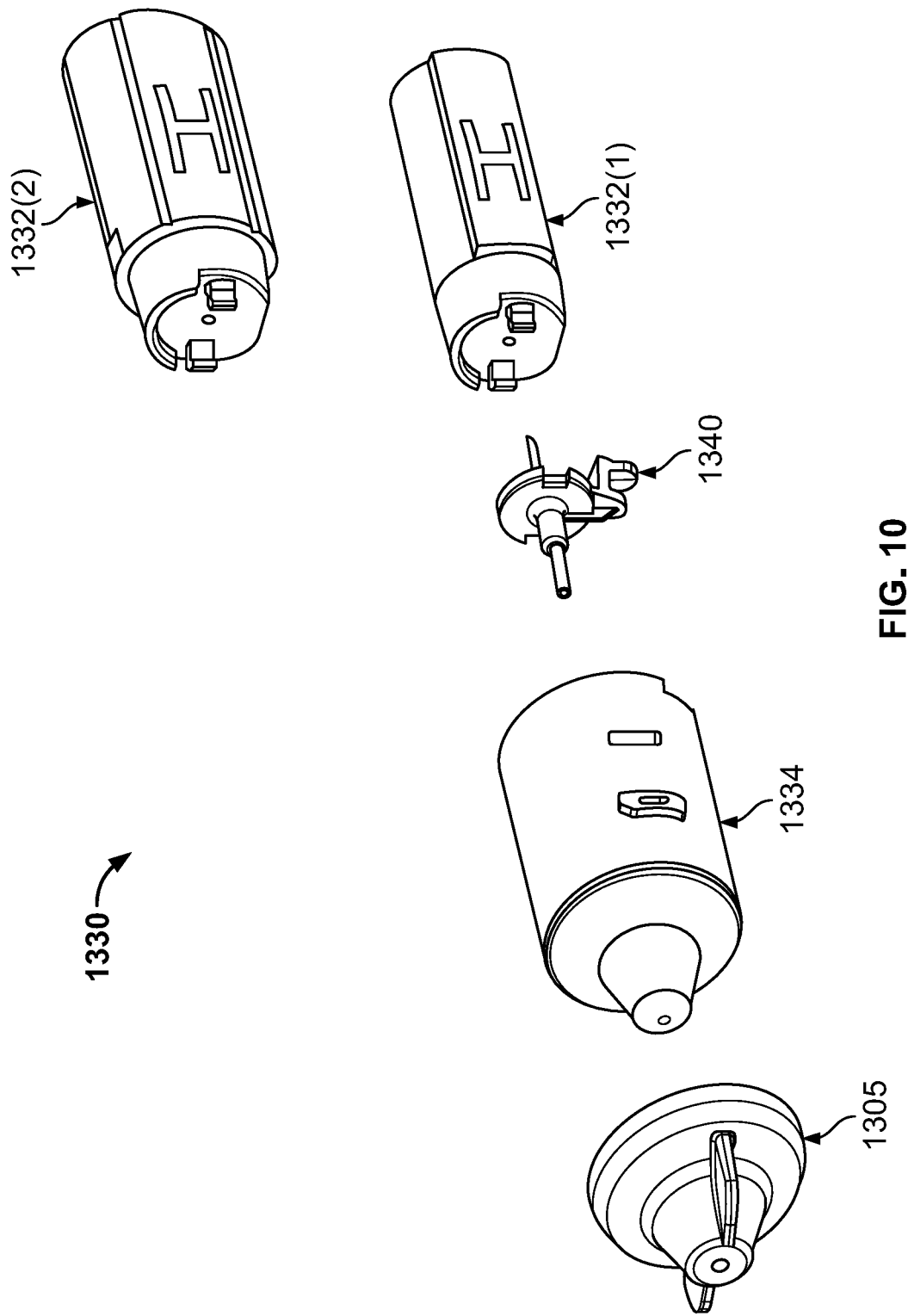

The semi-durable portion 1330 can be comprised of the nozzle 1334, the consumable portion housing 1332, and the electrode (or electrodes) 1340. Optionally, the electrode 1340, or a portion thereof, such as conductive base 1342, can be considered part of the nozzle 1334. Of course, as shown in FIGS. 7B and 8A-8C, the nozzle 1334, the electrode 1340, and the consumable portion housing 1332 may be separate components. As shown in FIG. 7B, an end of the tube 1341 may be provided at or adjacent to (i.e., recessed from) the nozzle tip 1335. In one or more embodiments, a kit may be provided with a plurality of consumable portion housings 1332 of different configurations (e.g., different sizes), each configured to be individually and securely received by the nozzle 1334, such as shown in FIG. 10 and FIG. 11. FIG. 11 also shows differently configured (e.g., different sizes) consumable portions 1350 to be received by corresponding consumable portion housings 1332.

The nozzle 1334, which in some instances may be interpreted as a housing, for instance, to house or hold the consumable portion housing 1332, can be configured to guide the semi-durable portion 1330 to a proper connection with the durable portion 1310, such that the semi-durable portion 1330 can receive high voltage to the electrode 1340 to create an electric field for application to the solution to electrospin or electrospray the solution from the nozzle tip 1335 toward the deposit surface. As noted above, the nozzle 1334 may also be configured to hold or provide an electrical connection, or portion thereof, to provide the high voltage to the electrode 1340. Also as noted above, in one or more embodiments of the disclosed subject matter, the nozzle 1334 may provide insulation for a portion of the high voltage path to the electrode 1340. The nozzle 1334 may be thermal plastic in one or more embodiments of the disclosed subject matter. Additionally or alternatively, the nozzle 1334 may be hydrophobic plastic.

Discussed above, the consumable portion housing 1332 can receive and hold the consumable portion 1350. The consumable portion housing 1332 can receive and hold the consumable portion 1350 when the consumable portion housing 1332 is already received by the nozzle 1334 or when the consumable portion housing 1332 has not yet been received by the nozzle 1334.

Figure 8A:
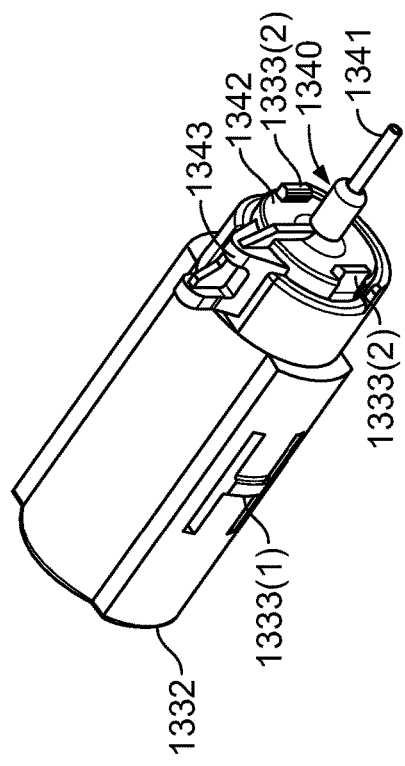
Figure 8B:
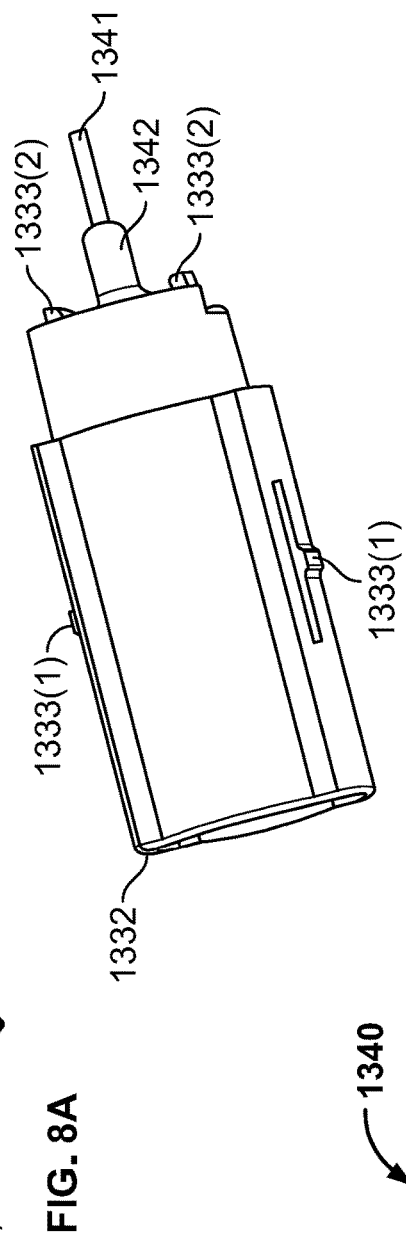

The consumable portion housing 1332 may include at least one fitting 1333(1). FIG. 8B, for instance, shows two fittings 1333(1). Each fitting 1333(1) can be configured to engage with a corresponding fitting 1337 of the nozzle 1334. Such fitting engagement can ensure that the consumable portion housing 1332 is properly inserted into the nozzle 1334. Further, such fitting engagement can form a lock to lock the consumable portion housing 1332 to the nozzle 1334. The lock can be released by actuation of the fitting 1333(1) and/or the side fitting 1337. For example, FIG. 8A shows "H-shaped" fittings 1333(1) with vertical projections. As shown in FIG. 7A, when the consumable portion housing 1332 is properly inserted into the nozzle 1334, the vertical projection of the fitting 1333(1) can be received into a vertical opening of the fitting 1337. Such engagement can lock the consumable portion housing 1332 in the nozzle 1334. To release the lock, the vertical projections of the fittings 1333(1) can be depressed, using a tool, for instance, to disengage the vertical projections from their respective vertical openings of the fittings 1337. The consumable portion housing 1332 may then be removed from the nozzle 1334. Of course, embodiments of the disclosed subject matter are not limited to the fittings 1333(1), 1337 shown in FIGS. 7A, 7C, 8A, and 8B. Other fitting configurations can be employed to lock and/or ensure proper insertion of the consumable portion housing 1332 into the nozzle 1334. As one example of an alternative fitting arrangement, the fittings on the consumable portion housing 1332 and the nozzle 1334 may be horizontal projections and openings, respectively. As another example of an alternative side fitting arrangement, the consumable portion housing 1332 may have one or more side longitudinal tracks that align with respective side track recesses of the nozzle 1334.

In one or more embodiments of the disclosed subject matter, the consumable portion housing 1332 may have at least one fitting 1333(2). FIGS. 8A and 8B show two fittings 1333(2), for example. The fittings 1333(2) can be received by fittings 1344 of electrode 1340. Thus, the electrode 1340, particularly the conductive base 1342 and the arm 1343, can be held to and against the consumable portion housing 1332. Put another way, the electrode 1340 can be removably coupled to the consumable portion housing 1332. In one or more embodiments, the fittings 1333(2) each can have a radially inward projection that extends over a surface of the conductive base 1342 when engaged in the fitting 1344. Thus, the electrode 1340 can be locked to the consumable portion housing 1332. To unlock the electrode 1340, the fittings 1333(2) may be pulled apart (i.e., radially outward) until the fittings 1333(2) disengage the conductive base 1342 and the electrode 1340 is able to be pulled apart from the consumable portion housing 1332.

The electrode 1440 may be comprised of the tube 1341 and the conductive base 1342. Optionally, the tube 1341 and the conductive base 1342 may be made of dissimilar materials. For example, the tube 1341 may be a conductive metal and the conductive base 1342 may be a conductive plastic. In one or more embodiments, the tube 1341 may be a hollow needle, a hollow electrode, or an elongate tube. Thus, the tube 1341 may serve as both a fluid path for the solution and a conductive surface to allow charge created by an electric field caused by the high voltage to be injected into the solution. More specifically, the tube 1341 may be hollow so as to receive solution from the container 1352 and output the solution at or just before the nozzle tip 1335. Generally, the flow path formed by the tube 1341 and the nozzle tip 1335 may be formed of materials that do not or do not substantially chemically or physio-chemically react with the solution in any substantial way.

As noted above, a first end of the tube 1341 may be pointed. A second end opposite the first end, for instance, adjacent the nozzle tip 1335, may not be pointed. The tube 1341 may be generally arranged in a center of the conductive base 1342. The conductive base 1342 can have the same polarity as the tube 1341. The electric field created by the conductive base 1342, which may be viewed as a separate electric field from the electric field of the tube 1341, may reduce lateral dispersion of the electrospun solution, which may make the web of electrospun fibers more targeted. Thus, the tube 1341 may be a first electrode, for instance, a primary electrode, and the conductive base 1342 may be deemed a second electrode, for instance, a secondary electrode.

Figure 8C:
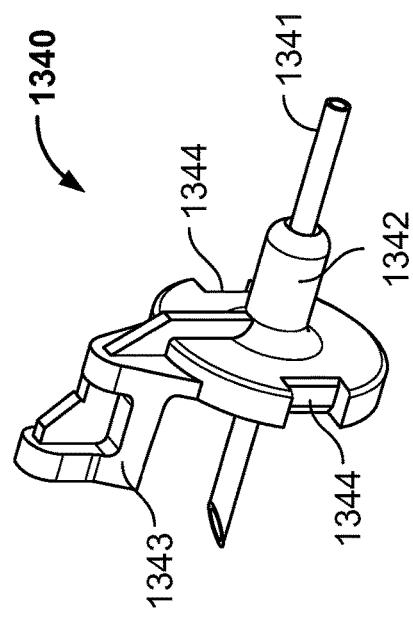

The conductive base 1342 may be in the form of a disc, plate-shaped, or a flange. Thus, in one or more embodiments of the disclosed subject matter, the conductive base 1432 may not be completely symmetrical. For example, FIGS. 7B, 8A, and 8C show conductive base 1342 having an arm 1343. As shown, the arm 1343 may extend at least radially outward from a longitudinal opening though which the tube 1341 is provided. The arm 1343 may also extend rearward, toward the durable portion 1310, particularly toward the high voltage line 1314. Further, as shown in FIGS. 4G and 4H, the arm 1343 can physically contact the contact 1317 when the semi-durable portion 1330 is removably coupled (properly) to the durable portion 1310. Thus, the arm 1343 forms a part of the electrical connection for the high voltage from the high voltage line 1314 to reach the electrode 1340 (including the tube 1341). Optionally, the conductive base 1432 may have a holding sleeve or sleeves extending from opposite surfaces of the conductive base 1432. The holding sleeve or sleeves may increase a friction fit with the tube 1341, which optionally may be removable from the conductive base 1432. In one or more embodiments, the conductive base 1432 may not be made entirely from conductive plastic. For example, conductive plastic may surround an underlying metal portion, in the form of a disc or plate, for instance, and the conductive plastic may extend 4 bars outward from an underlying metal portion. Such extending can strengthen the electric field pushing the fiber forward and so as to connect the electrode 1340 with the high voltage line, for instance, via arm 1343.

Figure 9:
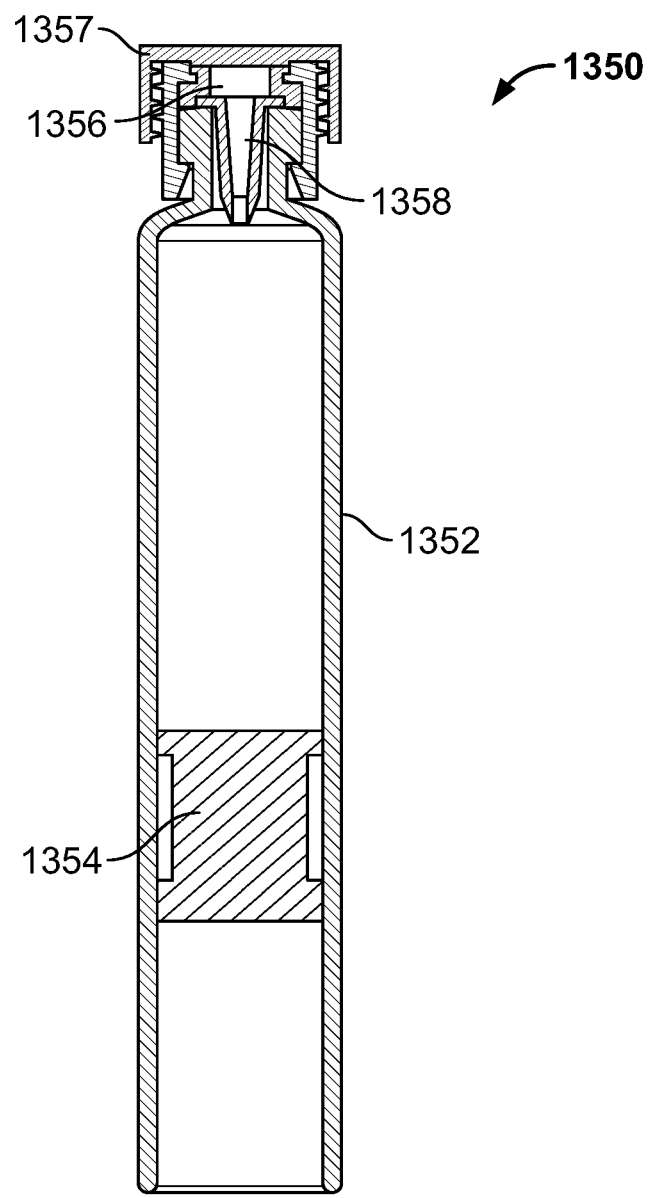

Turning to the consumable portion 1350, FIG. 6B shows a non-limiting example according to one or more embodiments of the disclosed subject matter, and FIG. 9 shows another non-limiting example according to one or more embodiments of the disclosed subject matter.

Generally, the consumable portion 1350 can include the closure 1356, the container 1352, and a piston or plunger 1354. The solution in the container 1352 may also be considered part of the consumable portion 1350.

As noted above, a boss of the actuator 1320 may be received in a recess of the container 1352, such that the boss abuts the plunger 1354. The boss can act on the plunger 1354, by way of movement of the actuator 1320, to cause the plunger 1354 to move inside the container 1352 and cause solution to be pushed toward and into the tube 1341 and ultimately output from the nozzle tip 1335. The solution can be stored in the container 1352 in a manner that limits atmospheric exposure until usage. For example, when the solution is to be used, the consumable portion 1350 can be inserted into the semi-durable portion 1330 such that a rear portion or end of the tube 1341 can puncture the closure 1356, which may be or include an airtight film or membrane over an opening to the container 1352 to form a fluid path between the bulk of the solution and an output at the nozzle tip 1335 via the tube 1341.

Alternatively, the closure 1356 may be in the form of a valve, such as shown in FIG. 9. The valve may operate so as to open upon connection of the consumable portion 1350 to the semi-durable portion 1330. Additionally or alternatively, the valve can regulate output of the solution to the nozzle tip 1335.

In the embodiment of FIG. 6B and the embodiment of FIG. 9, a seal cap 1357 may be provided. Optionally, the embodiment of FIG. 9 can have a conductive plastic portion 1358 below the closure 1356, inserted into the neck of the container 1352. Further, in the embodiment of FIG. 6B and the embodiment of FIG. 9, the semi-durable portion 1330 may have a first seal at the nozzle tip 1335 and a second seal at a portion of the flow path adjacent the conductive base 1342. For example, the first seal may be provided by the cap 1305, wherein a portion of the cap extends into the opening at the nozzle tip 1335, and the second seal may be provided by a closure 1356 in the form of a valve inside a tube opening adjacent the conductive base 1342.

The container 1352, which can be made of glass or plastic, can be configured to contain a predetermined maximum volume of the solution and output the solution to the electrode 1340 of the semi-durable portion 1330. For example, container 1352 can be sized to hold either 3 mL, 5 mL, or 10 mL as a maximum amount of solution. In one or more embodiments of the disclosed subject matter, the container 1352 may be a cartridge.

FIG. 10 is an exploded view of the semi-durable portion 1330 particularly showing the interchangeability of different consumable portion housings 1332 or holders for the semi-durable portion 1330. In particular, FIG. 10 illustrates that multiple different consumable portion housings 1332 can be used with the same nozzle 1334 and the same electrode 1340. More specifically, a first consumable portion housing 1332(1) may be provided for the nozzle 1334 and electrode 1340. Such consumable portion housing 1332(1) may be sized to receive a first consumable portion 1350 of a first size, for instance, a 3 mL size. The first consumable portion 1350 may be replaced in the consumable portion housing 1332(1) when empty or when the user simply wants to change to a different solution. The consumable portion housing 1332(1) may itself be replaced with a second consumable portion housing 1332(2), which may be sized to receive a second consumable portion 1350 of a second size, for instance, a 5 mL size. In one or more embodiments, a kit for the hand-held device 1300 may be provided with a plurality of consumable portion housings 1332(1), 1332(2).

Optionally, a plurality of different consumable portions 1350(1), 1350(2) may be provided as part of the kit or in any case usable with corresponding consumable portion housings 1332(1), 1332(2), respectively, such as shown in FIG. 11. Note also that the consumable portion housings 1332(1), 1332(2) of FIG. 11 have an insulating rod portion configured to receive an insulate a portion of the conductive rod 1315.

Figure 12C:
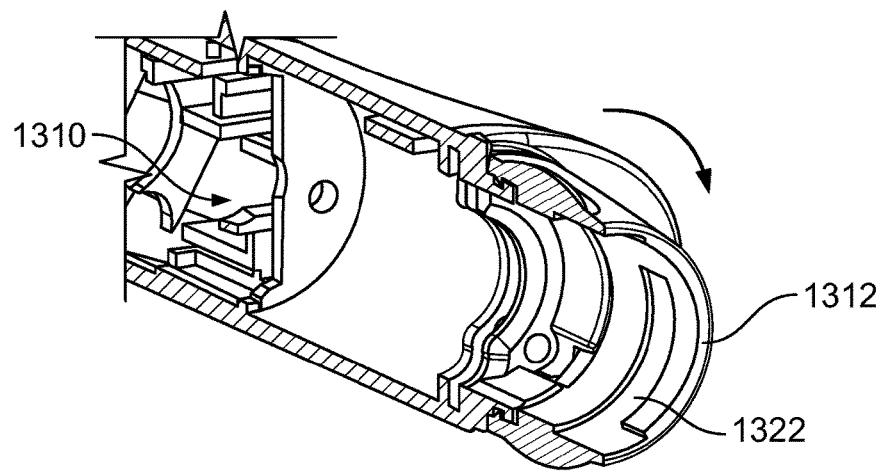

FIGS. 12A-12C illustrate insertion and locking aspects of the semi-durable portion 1330 and the durable portion 1310 according to one or more embodiments of the disclosed subject matter. Note that the semi-durable portion 1330 in FIGS. 12A and 12B is not identical to the semi-durable portion 1330 from previous figures.

As shown in FIG. 12A, the semi-durable portion 1330 can be longitudinally slid (i.e., right to left in FIG. 12A) into an open end of the durable portion 1310. Depending upon the configuration or current setting of the collar 1312, to insert the semi-durable portion 1330 into the durable portion 1310, the collar 1312 may need to be rotated to an open or unlocked position. Further, each of the at least one undercut or fitting 1338 may need to be aligned with a corresponding undercut or fitting 1332 of the collar 1312 in order to insert the semi-durable portion 1330 into the durable portion 1310. As noted above, as an example, the collar 1312 can be rotated by a predetermined amount, for instance, about 10 to about 60 degrees, preferably about 45 degrees, to the open or unlocked position (if it was not already in this position). In the embodiment shown, the conductive rod 1315 may extend from the nozzle 1334 and into and through a high voltage line opening at the open end of the durable portion 1310.

When the semi-durable portion 1330 is properly and fully seated in the durable portion 1310, such as shown in FIG. 12B, the conductive rod 1315 can high voltage contact an electrical contact of the durable portion 1310. Further, when the semi-durable portion 1330 is properly and fully seated in the durable portion 1310, such as shown in FIG. 12B, the collar 1312 may be rotated to a closed or locked position. As noted above, as an example, the collar 1312 can be rotated by a predetermined amount, for instance, about 10 to about 60 degrees, more preferably about 30 to about 60 degrees, and most preferably about 45 degrees, to the closed or locked position. Though the figures show a twist-lock using collar 1312, embodiments of the disclosed subject matter are not so limited. For example, the semi-durable portion 1330 may be inserted into and releasably locked with the durable portion 1310 via a slide-in snap lock configuration.

Figure 13:
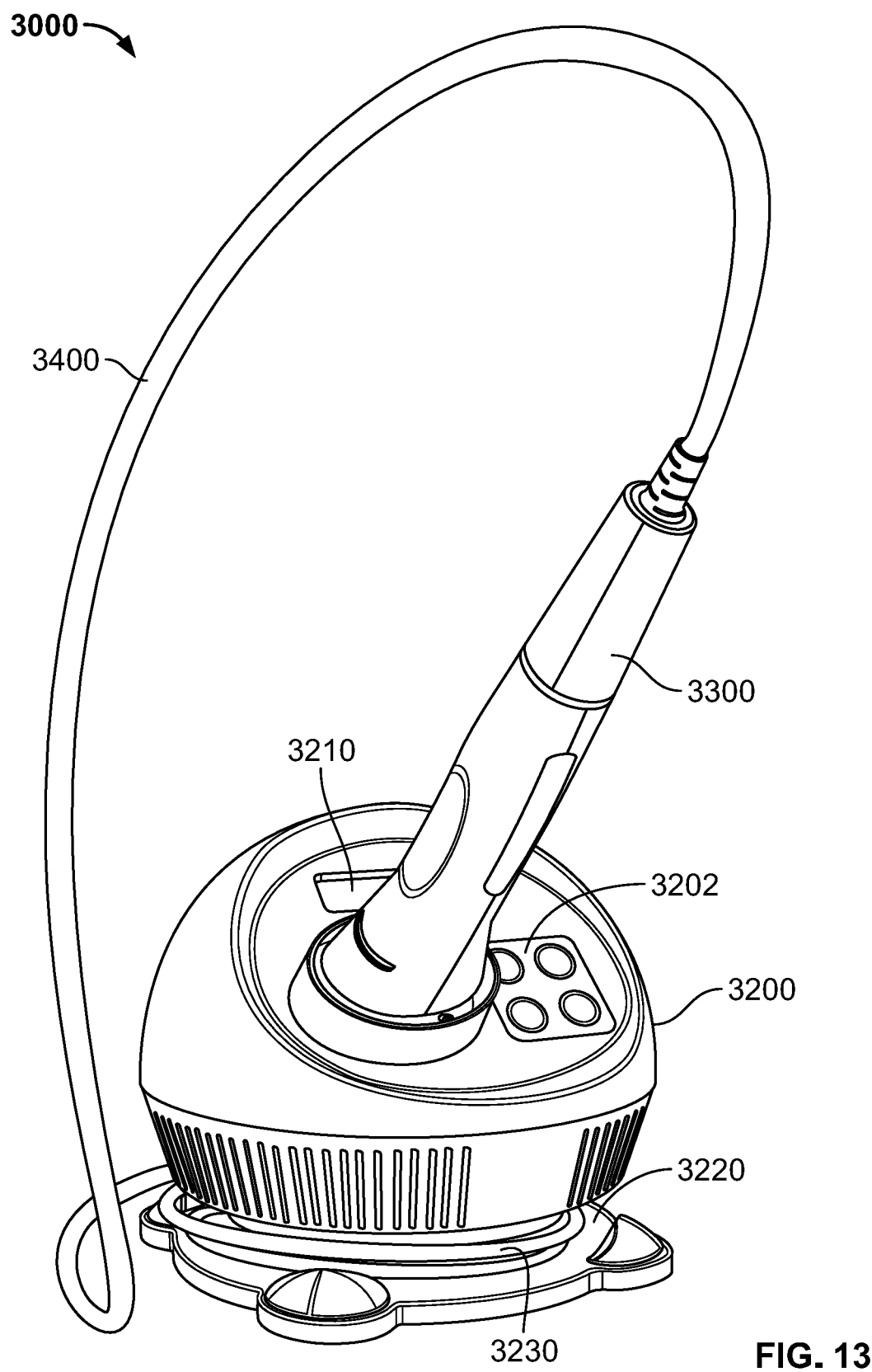
FIG. 13 is a perspective view of a system according to one or more embodiments of the disclosed subject matter.

FIG. 13 is a perspective view of a system 3000 according to one or more embodiments of the disclosed subject matter. Similar to the discussion above, the system 3000 can be comprised of a base station 3200 and a hand-held device 3300. A transmission medium 3400 can connect the base station 3200 to the hand-held device 3300. Additionally or alternatively, a wireless transmission medium may be provided between the base station 3200 and the hand-held device 3300.

Figure 14A:
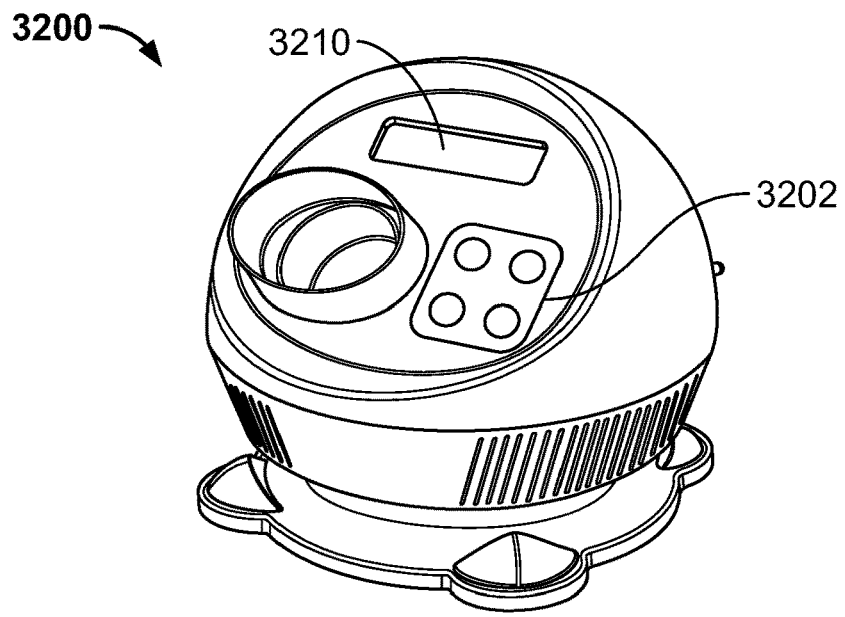
FIGS. 14A-14C show various views of a base station of the system of FIG. 13.
Figure 14B:
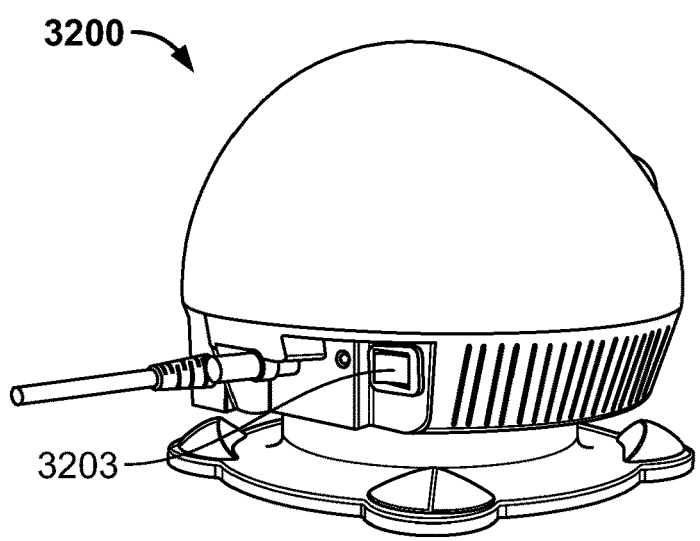
Figure 14C:
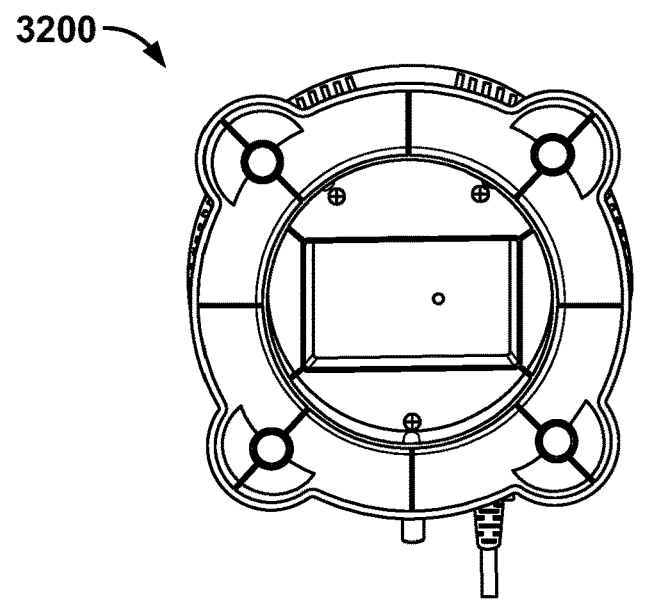

FIGS. 14A-14C show various views of the base station 3200. The base station 3200 may be configured and/or operate generally the same as the base stations discussed above. The base station 3200 can also have a receptacle 3220. The receptacle 3220 can be a recessed portion that extends entirely around the base station 3200, and can be configured to stow a power cable 3230, for instance. FIG. 13, for instance, shows the power cable 3230 being wrapped around the base station 3200 in the receptacle 3220. The base station 3200 can also include an insulation box 3225 therein, which can insulate the power supply and/or electrical components inside the base station 3200.

The base station 3200 can also include a control panel 3202. The control panel 3202 can receive inputs to control the hand-held device 3300. For instance, the control panel 3202 can provide panel buttons (e.g., four shown in FIG. 13 and FIG. 14A) to receive inputs from a user to control the hand-held device 3300. As used herein, such control can include the base station 3200 sending signals to the hand-held device 300 based on one or more inputs received at the control panel 3202. Optionally, power for the base station 3200 may be turned on and off via a switch 3203, which may be provided on a back side of the base station 3200, such as shown in FIG. 14B. In that the switch 3203 can turn off power to the base station 3200, the switch 3203 can turn off at least some of the power supplied to the hand-held device 3300 via the transmission medium 3400. Likewise, turning on the switch 3203 can provide at least some of the power supplied to the hand-held device 3300 from the base station 3200.

The control panel 3202 can also include a display 3210, such as a liquid crystal display (LCD) or light emitting diode (LED) display, which may be a touch screen or panel. The display 3210 may output information corresponding to operating characteristics of the hand-held device 3300, such as flow rate, an amount of high voltage received by the hand-held device 3300 or otherwise applied to the solution to perform electrospinning or electrospraying, a status of the hand-held device 3300, a direction of the motor of the handset, and/or whether appropriate grounding of the user is provided. Additionally or alternatively, the display 3210 may output information corresponding to operating characteristics of the base station 3200, such as an amount of high voltage supplied to the hand-held device 3300, the on/off state, whether the hand-held device 3300 is detected by the base station 3200 to be docked in a hand-held device receptacle, and/or whether power is supplied to the base station 3200 by an internal or external power source via the power cable 3230.

FIGS. 15A-15E show various views of the hand-held device 3300. The hand-held device 3300 may be configured and/or operate generally the same as the hand-held device discussed above. The hand-held device 3300, particularly a durable portion 3310 thereof, can include a body with a user control interface 1313 configured to receive manual input from the user to control output of the hand-held device 3300.

The durable portion 3310 can have the drive mechanism, which can be configured to cause the solution within a container of a consumable portion to be output to an electrode. The drive mechanism can include a motor and an actuator 3320. The motor of the drive mechanism may be a stepper motor, for instance, that drives the actuator 3320. Optionally, the actuator 3320 may be a linear actuator. The motor and actuator 3320 can be controlled based on operation of the user control interface 3313. Generally speaking, actuation of the actuator 3320, which may be in response to activation of the user control interface 3313, can drive a boss thereof against a plunger relative to a container that contains the solution to cause the plunger to move inside the container and cause solution in the container to be output from the container to the nozzle for application of high voltage and output from a nozzle tip as electrospun or electrosprayed solution. The double arrows in FIG. 15D (which is a cut-away view) shows exemplary forward and backward movement of the actuator 3320.

Figure 15A:
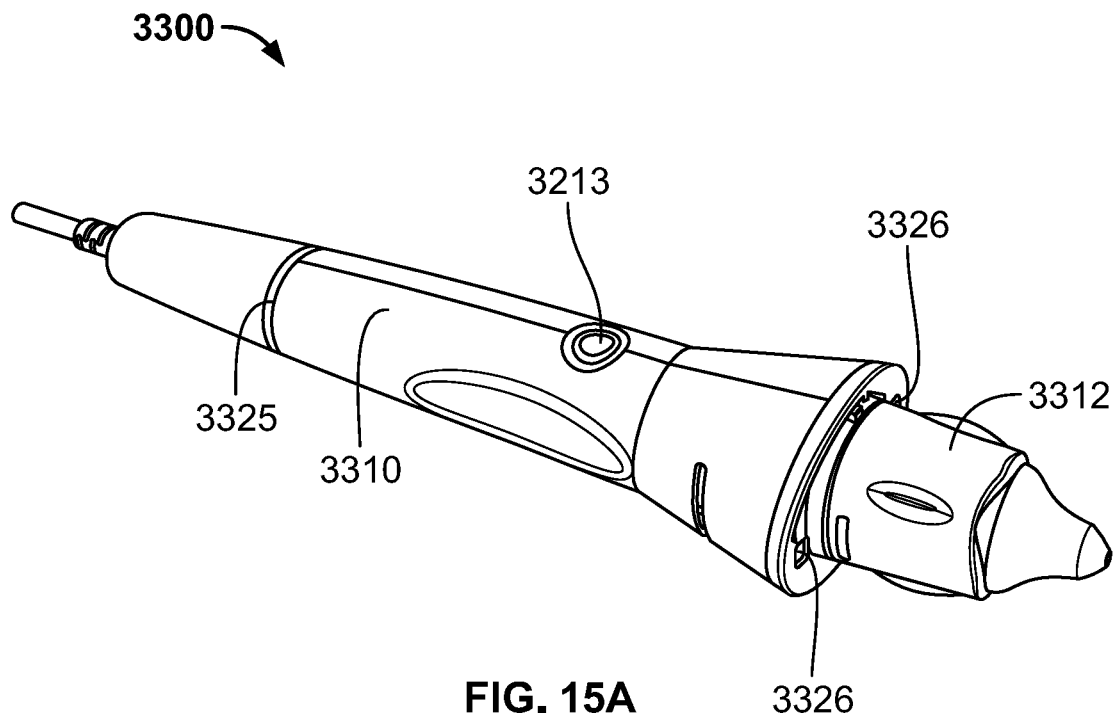
FIGS. 15A-15E show various views of a hand-held device of the system of FIG. 13.
Figure 15B:
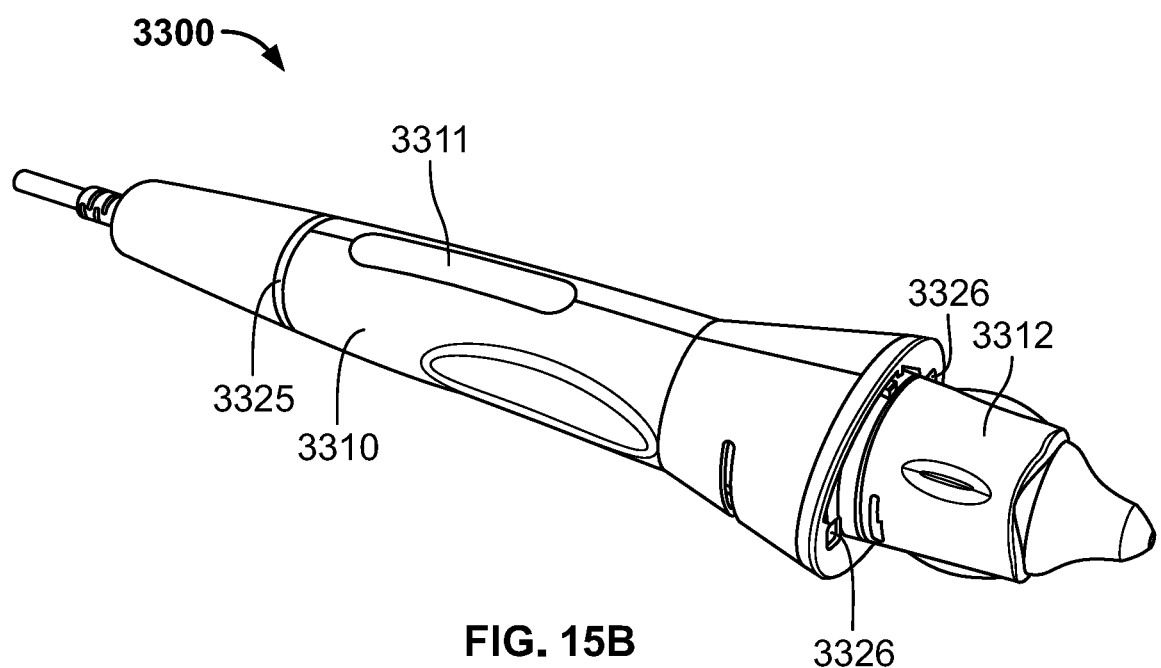
Figure 15C:
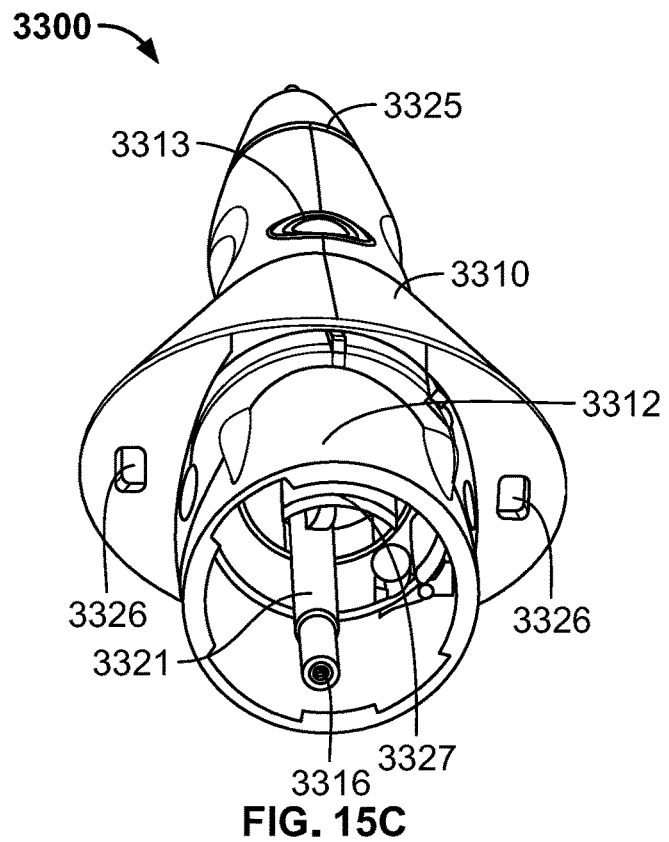
Figure 15D:
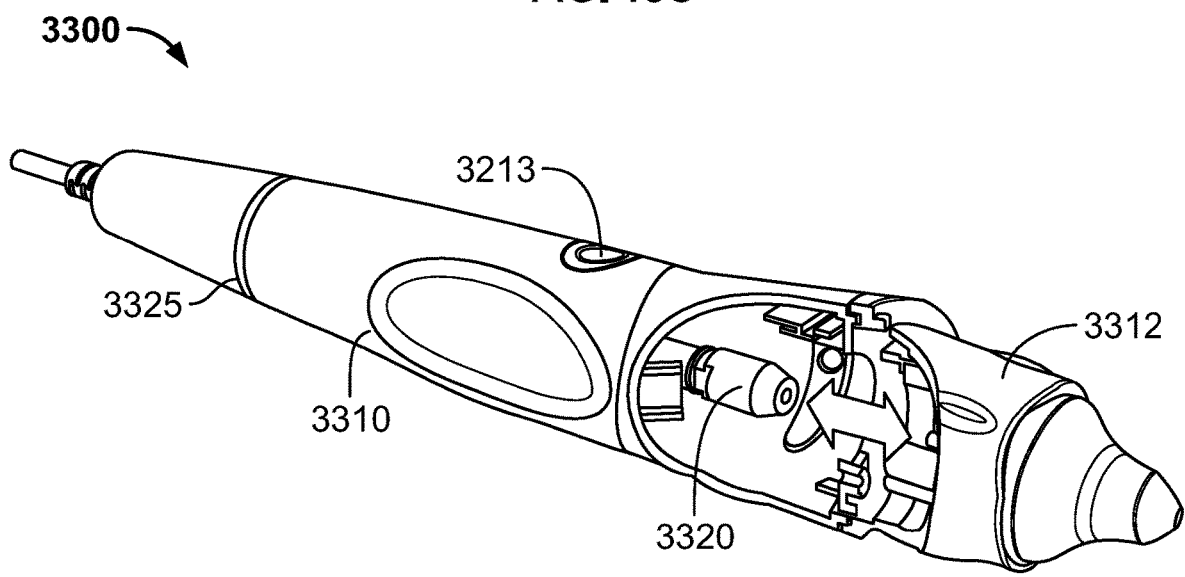

According to one or more embodiments of the disclosed subject matter, the hand-held device 3300, for instance, the durable portion 3310, can include an electrically conductive portion 3311. The electrically conductive portion 3311 can be provided on a side of the durable portion 3310 different from a side at which the user control interface 1313 is provided, such as on the opposite side as shown in FIG. 15B. Additionally, according to one or more embodiments, the electrically conductive portion 3311 can be longitudinally offset from the user control interface 1313. For instance, the electrically conductive portion 3311 can be closer to a distal end of the hand-held device 3300 than the user control interface 1313 and/or farther from the proximal end of the hand-held device 3300 than the user control interface 1313. The electrically conductive portion 3311 can also be a different shape as compared to the user control interface 1313. For instance, FIGS. 15A and 15B show, as non-limiting examples, the electrically conductive portion 3311 being elongate and the user control interface 1313 being circular.

The electrically conductive portion 3311 can be made of metal or metal- or metallic-plated resin. During operation of the hand-held device 3300, a user's hand can come into contact with the electrically conductive portion 3311. The user's hand can also operate the user control interface 1313. Thus, the user can hold the durable portion 3310 with one hand and contact both the user control interface 1313 and the electrically conductive portion 3311. In general, the electrically conductive portion 3311 can be configured to pass relatively weak electricity to ground via the user's body when the user operates the hand-held device 3300 via the user control interface 1313 and contacts the electrically conductive portion 3311. According to one or more embodiments of the disclosed subject matter, the electrically conductive portion 3311 is not connected to a high voltage source that applies a high voltage to the nozzle of the hand-held device 3300. For example, the electrically conductive portion 3311 and the high voltage source may have "false grounds," but the ground or neutral of the power supply may not be directly connected to the electrically conductive portion 3311.

The durable portion 3310 can also include a light source 3325. The light source 3325 may be comprised of one or more lights, such as one or more LEDs. The one or more lights can individually or separately be controlled to change colors and/or flash. For instance, a color or colors of the light(s) of the light source 3325 can change colors and/or flash to indicate a status of the system 3000, such as a status of the hand-held device 3300 and/or the base station 3200. According to one or more embodiments, the light source 3325 can be in the form of a light ring, such as shown in FIGS. 15A-15D.

The durable portion 3310 can also include one or more sensors 3326. The one or more sensors 3326 can be configured to determine distance from the hand-held device 3300 to an application surface, such as a user's skin. Optionally, the one or more sensors 3326 can be time-of-flight (TOF) sensors. Signals from the one or more sensors 3326 can be used to control the hand-held device 3300. For instance, the feedback from the one or more sensors 3326 can cause the light source 3325 to change characteristics (e.g., blink, change colors) to indicate proper and/or improper distance. In one or more embodiment, the feedback from the one or more sensors 3326 can be used to control output of the solution from the hand-held device 3300. For instance, if the hand-held device 3300 is detected to be too close and/or too far away from the application surface, control circuitry of the hand-held device 3300 can stop or prevent the output of electrospray or electrospun solution.

Figure 15E:
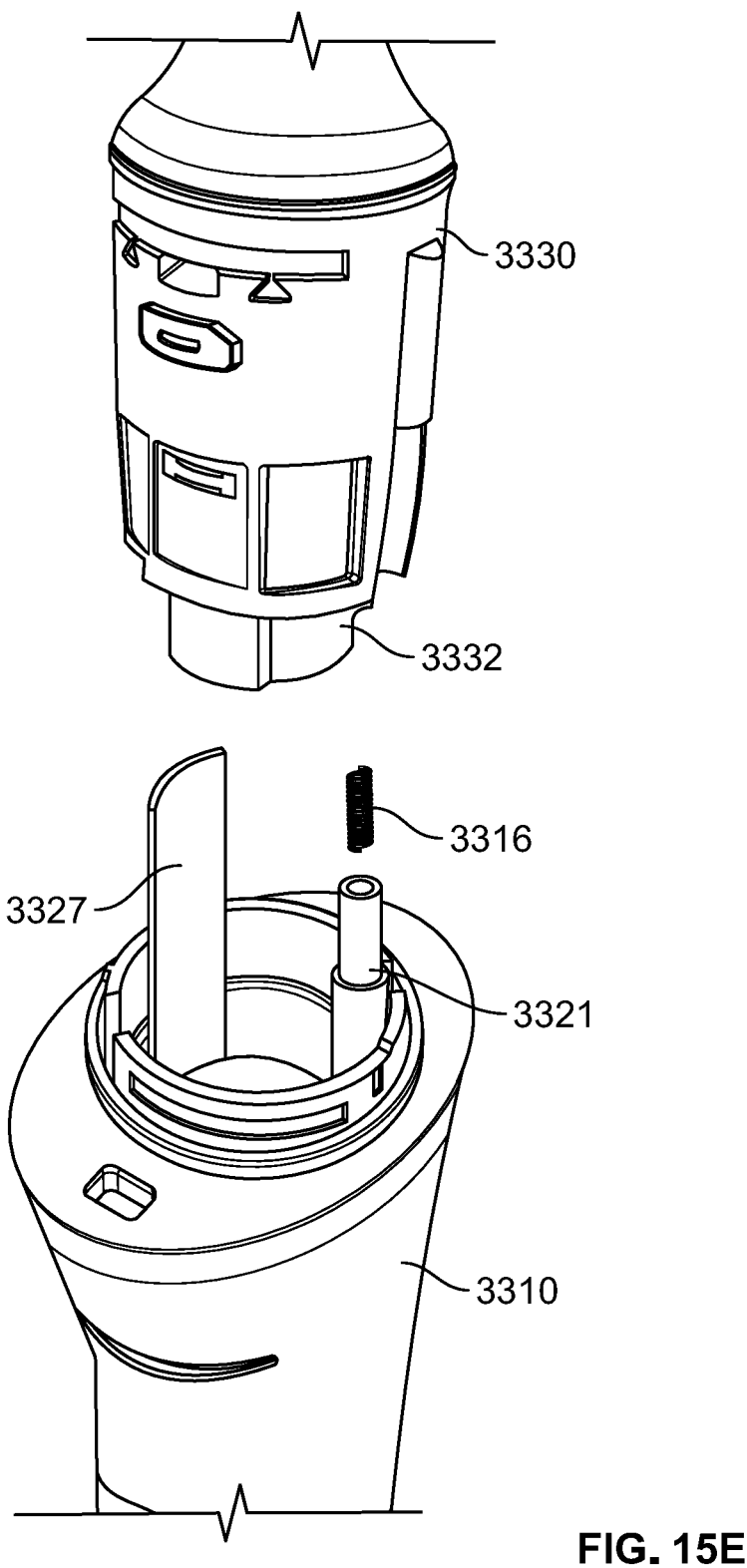
Figure 16:
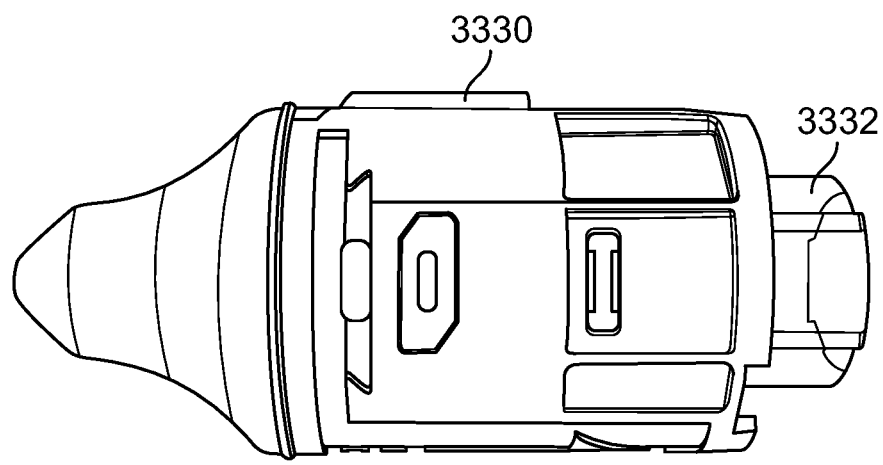
FIG. 16 and FIG. 17 are side views of a semi-durable portion and a consumable portion according to one or more embodiments of the disclosed subject matter.
Figure 17:
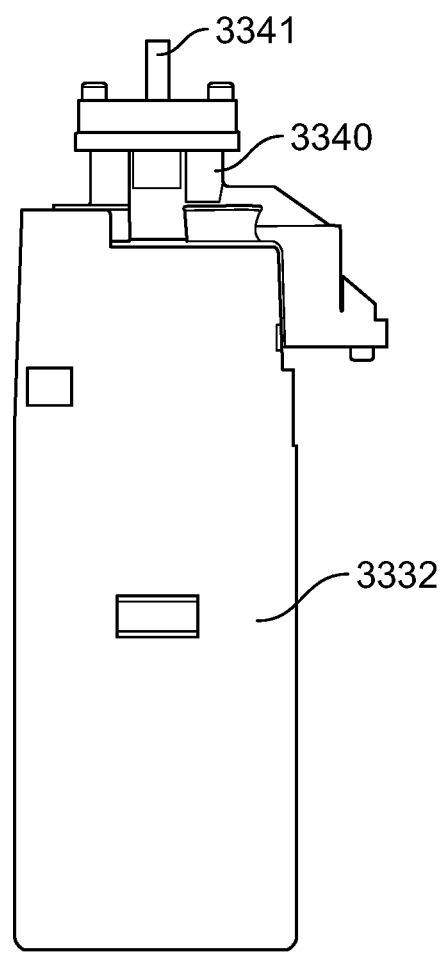

The durable portion 3310 can include a guide 3327 for attachment of the semi-durable portion 3330. As shown in FIG. 15E, for instance, the guide 3327 can have a projection that extends from an end of the durable portion 3310. A recess associated with the guide may be provided at a radially outward bottom portion of the guide 3327. The semi-durable portion 3330 can have a sidewall configured to receive the projection of the guide 3327. A bottom portion of the sidewall of the semi-durable portion 3330 can be configured to be seated in the recess. FIG. 18 shows an example of the semi-durable portion 3330 removably coupled to the durable portion 3310, wherein the semi-durable portion 3330 is positioned relative to the guide 3327 and the recess. Note also that the guide 3327 can be between a portion of the sidewall of the semi-durable portion 3330 and an outer wall of a consumable portion housing 3332 configured to house a consumable portion. The guide 3327 and corresponding portion of the semi-durable portion 3330 can be used to reliably align and connect the semi-durable portion 3330 to the durable portion 3310. Optionally, the guide 3327 can be an anti-rotation projection (e.g., bar) configured to prevent rotation of the semi-durable portion 3330 relative to the durable portion 3310. In particular, the guide 3327 can be provided in a slot of the sidewall of the semi-durable portion 3330 such that lateral sides of the guide 3327 abut the sidewall and prevent the semi-durable portion 3330 from rotating.

An electrode connection rod 3321, which may be made of insulation material (e.g., plastic), can also extend from the durable portion 3310. Generally, the electrode connection rod 3321, via internal electrically conductive components thereof, can provide a voltage source (e.g., high voltage) from the durable portion 3310 to the semi-durable portion 3330, particularly an electrode 3340 thereof. The electrode connection rod 3321 can include a an elastic member (e.g., spring) 3316 therein. As shown in FIG. 18, the elastic member 3316 can extend in a same direction as the body of the semi-durable portion 3330. Moreover, the elastic member 3316 can be provided radially inward of the sidewall of the semi-durable portion 3330 and inside of a collar 3312, which can be rotatable to lock or release the semi-durable portion 3330 from connection with the durable portion 3310. Thus, the connection and corresponding pathway for the voltage from the durable portion 3310 to the semi-durable portion 3330 can be provided so as to minimize a thickness of the outputting end of the hand-held device 3300. Additionally, the bias of the elastic member 3316 can ensure a reliable mechanical and hence electrical connection between an arm 3343 of the electrode 3340 and an electrical connector (e.g., conducting rod, contact) at the other side of the elastic member 3316 for providing the voltage to the electrode 3340.

Referring to FIGS. 18-19C, the electrode 3340 can have a conductive base 3342 and the arm 3343, as noted above. Optionally, the conductive base 3342 can have one or more fittings for mating with other portions of the semi-durable portion 3330, such as the consumable portion housing 3332. FIGS. 19A-19C, for instance, show two fittings 3344.

Generally, the electrode 3340 can provide an electrical connection between the hollow elongate portion 3341 and the voltage from the durable portion 3310 via the elastic member 3316 and other electrically conductive components associated with the electrode connection rod 3321. The configuration of the electrode 3340 can assist with the spraying or spinning of fiber relatively straight by creating a relatively even electric field.

According to one or more embodiments, the electrode 3340, or the conductive base 3342 thereof, can be referred to as a disc electrode. Moreover, according to one or more embodiments, the conductive base 3342 can have one or more plate or planar portions. Thus, embodiments of the disclosed subject matter can have one or more disc electrode portions. For instance, FIGS. 19A-19C show the conductive base 3342 having a first planar portion 3345 and a second planar portion 3346. A hollow elongate portion 3341, for instance, a needle or tube electrode, can extend through the center of the conductive base 3342, such as shown in FIGS. 19A and 19B. Optionally, the hollow elongate portion 3341 can extend from only one side of the electrode 3340, for instance, from the outward-facing face of the first planar portion 3345 (i.e., face intended to face toward the consumable portion housing 3332), whereas the other end of the hollow elongate portion 3341 can be flush, for instance, with the (i.e., face intended to face away from the consumable portion housing 3332). The electrode 3340, with the exception of the hollow elongate portion 3341, can be formed in one piece (e.g., a single-molded component). Thus, the conductive base 3342, including the first planar portion 3345, the second planar portion 3346, and the body portion therebetween, can be integral with each other. Moreover, the conductive base 3342 can be made from a same material.

In that the outward-facing face of the first planar portion 3345 (i.e., face intended to face toward the consumable portion housing 3332) can be flat, such as particularly shown in FIGS. 19B and 19C, the electrode 3340 can prevent leakage of the solution from the consumable portion when the consumable portion is properly installed relative to the consumable portion housing 3332. That is, the flat face of the outward-facing face of the first planar portion 3345 can create a seal around the hollow elongate portion 3341 at an interface between the first planar portion 3345 and the consumable portion housing 3332. Optionally, as shown in FIG. 18, a sealing structure 3360 can be provided on the outward-facing face of the second planar portion 3346, around the hollow elongate portion 3341. In general, the sealing structure 3360 can operate as a gasket, for instance, to seal around the hollow elongate portion 3341 and a hollow projection of the nozzle that interfaces with the hollow elongate portion 3341. According to one or more embodiments, the sealing structure 3360 can be flexible and can also provide cushioning or padding around the hollow elongate portion 3341, for instance, for the hollow projection of the nozzle.

The first planar portion 3345 and the second planar portion 3346 can be cylindrical/generally cylindrical or circular/generally circular in front or rear views of the electrode 3340. According to one or more embodiments, the first planar portion 3345 and the second planar portion 3346 can be different configurations (e.g., size, shape, etc.). For instance, FIGS. 19A-19C show the second planar portion 3346 being smaller in size (e.g., diameter, circumference, etc.) than the first planar portion 3345. Optionally, the body portion between the first planar portion 3345 and the second planar portion 3346 can be smaller in size (e.g., diameter, circumference, etc.) than the first planar portion 3345 and/or the second planar portion 3346. Additionally, as noted above, the outward-facing face of the first planar portion 3345 (i.e., face intended to face toward the consumable portion housing 3332) can be flat, whereas the outward-facing face of the second planar portion 3346 (i.e., face intended to face away from the consumable portion housing 3332) can have one or more surface features.

The arm 3343 can extend radially outward from at least the first planar portion 3345. For instance, FIGS. 19A-19C show the arm 3343 extending radially outward from the first planar portion 3345 and the body portion between the first planar portion 3345 and the second planar portion 3346. The arm 3343 may also extend in a longitudinal direction of the electrode 3340. For example, FIG. 19C shows the arm 3343 extending longitudinally in a same direction as the outward-facing face of the first planar portion 3345.

For instance, the second planar portion 3346 can have one or more projections 3347 extending from the outward-facing face thereof. FIGS. 19A-19C, for instance, show two projections 3347, though other embodiments may have a different number, such as four. Optionally, the projections 3347 may be symmetrically arranged on the outer face of the second planar portion 3346. For example, FIG. 19C shows the projections 3347 being offset from each other by 180 degrees, on opposite sides of the outer face of the second planar portion 3346. The projections 3347 can be of the same configuration or different. For example, according to one or more embodiments the projections 3347 can be cylindrical or rectangular (including generally rectangular), such as shown in FIGS. 19A-19C. In one or more embodiments the projections 3347 may taper slightly away from the outer face of the second planar portion 3346.

Figure 20:
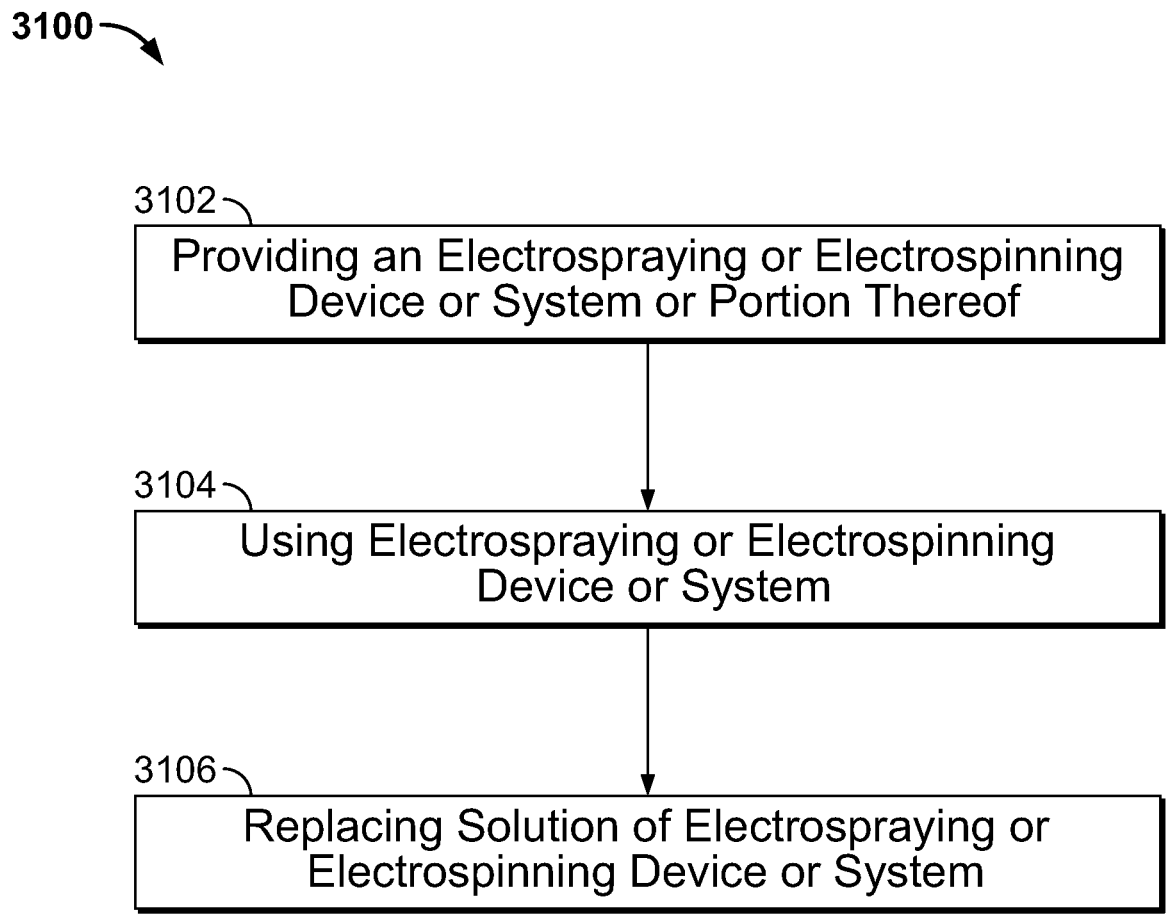
FIG. 20 is a flow chart of a method according to one or more embodiments of the disclosed subject matter.

FIG. 20 is a flow chart of a method 3100 according to one or more embodiments of the disclosed subject matter.

The method 3100 can be comprised of providing an electrospraying or electrospinning device or system or a portion or portions thereof according to one or more embodiments of the disclosed subject matter 3102. The providing can constitute the entirety of the method 3100.

In one or more embodiments, the provided portion may be a solution, for instance, in spraying format, for the electrospraying or electrospinning device or system or portion thereof. For example, a spinning formulation for the solution can be comprised of a volatile solvent selected from alcohol and ketone, polymer with fiber forming ability, and water, preferably alcohol, water insoluble polymer, and water, more preferably ethanol, polymer with fiber forming ability selected from polyvinyl butyral, polyurethane, and partially saponified polyvinyl alcohol, and water. The water insoluble polymer with fiber forming ability can be selected from one or more of completely saponified polyvinyl alcohol, which can be insolubilized after the fiber formation; partially saponified polyvinyl alcohol, which can be cross-linked after the fiber formation when used in combination with a cross-linking agent; oxazoline modified silicone, such as a poly(N-propanoylethyleneimine)-grafted dim ethyl siloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyurethane resin; a polyethylene terephthalate resin; a polybutylene terephthalate resin; a polyurethane resin; a polyamide resin; a polyimide resin; and a polyamideimide resin, and the like. Of course, this is but one non-limiting example of a spinning formulation for the solution.

Polymers having fiber formation ability are roughly classified into water-soluble polymers and water insoluble polymers. The term "water soluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, 0.5 g or more of the immersed polymer dissolves in the water. On the other hand, the term "water insoluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, more than 0.5 g of the immersed polymer does not dissolve in the water.

From the viewpoint of improving fiber forming ability, the content of the polymer of the spinning formulation for the solution is preferably 6 mass % or more, and even more preferably 8 mass % or more, and preferably 30 mass % or less. The content of sum of alcohol, ketone, and water is preferably 50 mass % or more and preferably 92 mass % or less.

The method 3100 can additionally or alternatively be comprised of using an electrospraying or electrospinning device or system according to one or more embodiments of the disclosed subject matter 3104. Using the electrospraying or electrospinning device or system can constitute the entire method 3100. Alternatively, using the electrospraying or electrospinning device or system can be performed in conjunction with the provided electrospraying or electrospinning device or system according to 3102.

The method 3100 may also be comprised of replacing the solution of the electrospraying or electrospinning device or system or portion thereof. Such replacing can involve replacing a consumable portion in a consumable portion housing with another consumable portion of a same configuration (e.g., size and/or shape), but not necessarily with the same type of solution. Alternatively, replacing can involve replacing a consumable portion and a consumable portion housing and with another set of consumable portion and consumable portion housing of a different configuration (e.g., size and/or shape), but not necessarily with different solutions. For example, a 2 mL consumable portion container may be replaced with a 5 mL consumable portion container. The replacing can be performed prior to and/or after the using of the electrospraying or electrospinning device or system or portion thereof at 3104.

Embodiments of the disclosed subject matter may provide for an electrospinning or electrospraying process that may be functionally independent of orientation of a solution output device, particularly a portable, hand-held solution output device, and may be positioned to output solution on a deposit surface in relatively difficult areas, such as a particularly difficult area of a human's body. Also, embodiments of the disclosed subject matter can implement a modular construction, allowing multiple physical configurations, types of solution, and/or solution output characteristics. Additionally, embodiments of the disclosed subject matter can allow for solution to be readily replaced without contamination between samples.

Embodiments of the disclosed subject matter may also be as set forth according to the parentheticals in the following paragraphs.

(1) A portable, hand-held device for electrospinning or electrospraying toward a deposit surface a predetermined solution formulated for the device, the device comprising: a durable portion; a semi-durable portion; and a consumable portion, wherein the consumable portion is removably coupled to the semi-durable portion, wherein the semi-durable portion is removably coupled to the durable portion, wherein the durable portion is configured to provide a high voltage to the semi-durable portion and includes: a drive mechanism configured to cause the solution within a container of the consumable portion to be output to at least one electrode of the semi-durable portion, and a user control interface configured to receive manual input from a user to control the drive mechanism and application of the high voltage to the at least one electrode to create an electric field for application to the solution to electrospin or electrospray the solution from a nozzle of the semi-durable portion toward a deposit surface, wherein the semi-durable portion is configured to provide the high voltage to the at least one electrode and includes: the nozzle, which is configured to output the solution from a nozzle tip thereof, and the at least one electrode, which is inside the nozzle, and wherein the consumable portion includes: the container, which is configured to contain a predetermined maximum volume of the solution and output the solution to the at least one electrode of the semi-durable portion.

(2) The device according to (1), wherein the at least electrode is hollow.

(3) The device according to (1) or (2), wherein a portion of the at least electrode is hollow.

(4) The device according to any one of (1) to (3), wherein the at least one electrode is a hollow elongate tube.

(5) The device according to any one of (1) to (4), wherein the container of the consumable portion is sealed and configured to receive the semi-durable portion via the at least one electrode.

(6) The device according to any one of (1) to (5), wherein the container of the consumable portion is sealed and configured to receive the semi-durable portion via the at least one electrode, which is in the form of a hollow tube.

(7) The device according to any one of (1) to (6), wherein the consumable portion is sealed at an end proximal to the semi-durable portion via a valve that opens upon connection with the semi-durable portion.

(8) The device according to any one of (1) to (7), wherein the consumable portion is sealed at an end proximal to the semi-durable portion via a membrane configured to be punctured upon connection with the semi-durable portion.

(9) The device according to any one of (1) to (8), wherein the consumable portion is configured to receive the electrode of the semi-durable portion when the consumable portion is removably coupled to the semi-durable portion.

(10) The device according to any one of (1) to (9), wherein the semi-durable portion includes a fitting portion between the consumable portion and the durable portion.

(11) The device according to any one of (1) to (10), wherein the semi-durable portion includes a holder configured to hold a first end of the consumable portion when the consumable portion is removably coupled to the semi-durable portion.

(12) The device according to any one of (1) to (11), wherein the holder holds the first end of the consumable portion such that a second end of the consumable portion extends from the semi-durable portion.

(13) The device according to any one of (1) to (12), wherein a length associated with the first end that is held by the holder and proximal to the semi-durable portion is greater than a length associated with the second end of the consumable portion that extends from the semi-durable portion.

(14) The device according to any one of (1) to (13), wherein a length associated with the first end that is held by the holder and proximal to the semi-durable portion is less than a length associated with the second end of the consumable portion that extends from the semi-durable portion.

(15) The device according to any one of (1) to (14), wherein said holder is configured to be removable from the semi-durable portion and replaced with another holder, having a configuration different from a configuration of said holder, that is configured to hold another consumable portion having a configuration different from a configuration of said consumable portion.

(16) The device according to any one of (1) to (15), wherein the nozzle of the semi-durable portion is configured to receive said holder and another holder having a configuration different from a configuration of said holder.

(17) The device according to any one of (1) to (16), wherein, when the consumable portion is removably coupled to the semi-durable portion and the semi-durable portion is removably coupled to the durable portion, a first end of the consumable is inside the semi-durable portion and a second end of the consumable opposite the first end is inside the durable portion.

(18) The device according to any one of (1) to (17), wherein the consumable includes a cap, the container, and a piston.

(19) The device according to any one of (1) to (18), wherein the container is made of glass or plastic.

(20) The device according to any one of (1) to (19), wherein the nozzle is configured to: guide the semi-durable to a proper connection with the durable portion such that the semi-durable portion is removably coupled to the durable portion to enable the application of the high voltage to the electrode to create the electric field for application to the solution to electrospin the solution from the nozzle tip of the semi-durable portion toward the deposit surface, hold a portion of an electrical connection part to provide the high voltage to the electrode, and/or insulate a portion of a high voltage electrode configured to provide the high voltage through the semi-durable portion to the electrode.

(21) The device according to any one of (1) to (20), wherein the at least one electrode in the nozzle includes a hollow tube portion and an extending portion that extends in a circumferential direction of the tubular portion.

(22) The device according to any one of (1) to (21), wherein an electrical connection extends from one end of the semi-durable portion to a nozzle side and continues to the extending portion.

(23) The device according to any one of (1) to (22), wherein the electrical connection is positioned on an outer circumference side of a holder for the consumable portion.

(24) The device according to any one of (1) to (23), wherein the electrical connection includes a spring.

(25) The device according to any one of (1) to (24), wherein the semi-consumable portion includes a consumable portion housing, the consumable portion housing including an insulated rod configured to house a high voltage electrode, the insulated rod extending from an end of the semi-durable portion opposite the nozzle tip.

(26) The device according to any one of (1) to (25), wherein the semi-durable portion includes a lock configured to mate with a receptacle of the durable portion to lock the semi-durable portion in an operating position with the durable portion.

(27) The device according to any one of (1) to (26), wherein the lock is biased to one of an unlocked position where the semi-durable portion is uncoupleable from the durable portion and a locked position where the semi-durable portion is not uncoupleable from the durable portion.

(28) The device according to any one of (1) to (27), wherein the durable portion includes a detector configured to detect proper connection of the semi-durable portion in the operating position to the durable portion.

(29) The device according to any one of (1) to (28), wherein the lock is a slide-in snap lock.

(30) The device according to any one of (1) to (29), wherein the lock is a twist lock.

(31) The device according to any one of (1) to (30), further comprising a twist lock in the form of an about 10 to about 60 degrees twist lock, the twist lock including a collar rotatably coupled to the durable and configured to rotate about 10 to about 60 degrees to engage and disengage with the semi-durable when the semi-durable portion is removably coupled to the durable portion.

(32) The device according to any one of (1) to (31), wherein the semi-durable and/or the collar each is a color configured to prevent or minimize unwanted feedback to a time of flight (TOF) sensor of the device.

(33) The device according to any one of (1) to (32), wherein the color is black.

(34) The device according to any one of (1) to (33), wherein the semi-durable portion is slidable onto an end of the durable portion in a longitudinal axis direction of the durable portion.

(35) The device according to any one of (1) to (34), wherein the consumable portion is removably coupled to the semi-durable portion prior to the semi-durable portion being removably coupled to the durable portion.

(36) The device according to any one of (1) to (35), wherein, when the semi-durable portion is connected with the durable portion, an outer peripheral surface of the semi-durable portion is exposed to the outside.

(37) The device according to any one of (1) to (36), wherein the durable portion includes a cartridge detection switch configured to detect when the consumable portion is removably coupled to the semi-durable portion when the semi-durable portion is removably coupled to the durable portion.

(38) The device according to any one of (1) to (37), wherein the nozzle is configured to be removably coupled to a cartridge housing configured to be removably coupled to the consumable portion and separately another cartridge housing configured to be removably coupled to another consumable portion, said cartridge housing and said consumable portion being different in type, size, and/or shape from said another cartridge housing and said another consumable portion.

(39) The device according to any one of (1) to (38), wherein the nozzle is thermal plastic.

(40) The device according to any one of (1) to (39), wherein the nozzle is hydrophobic plastic.

(41) The device according to any one of (1) to (40), wherein the user control interface includes a trigger button to receive the manual input from the user, the trigger button being connected to ground.

(42) The device according to any one of (1) to (41), wherein the semi-durable portion includes a first seal at the nozzle tip and a second seal at a portion of the flow path adjacent an extending electrode.

(43) The device according to any one of (1) to (42), wherein the semi-durable portion includes a valve in the flow path configured to regulate output of the solution from the nozzle.

(44) The device according to any one of (1) to (43), wherein the consumable portion includes the container in the form of a cartridge, a cap, and a piston.

(45) The device according to any one of (1) to (44), wherein the semi-durable portion and/or the durable portion each has at least one attachment arrangement configured to detachably hold an accessory.

(46) The device according to any one of (1) to (45), further comprising a high voltage (HV) line to provide the high voltage from the durable portion to the semi-durable portion, the HV line being surrounded by insulation of the semi-durable and/or insulation of the durable.

(47) The device according to any one of (1) to (46), wherein the insulation is non-conductive plastic.

(48) The device according to any one of (1) to (47), wherein the HV line is configured to be connected to an electrical contact of the durable portion via a slide-in electrical connection, such slide-in electrical connecting involving the HV line being slid in a longitudinal direction thereof to connect with the electrical contact of the durable portion.

(49) The device according to any one of (1) to (48), wherein the semi-durable portion is configured to be slid into an opening of the durable portion so as to be removably coupled to the durable portion.

(50) The device according to any one of (1) to (49), further comprising: a high voltage (HV) line to provide the high voltage from the durable portion to the semi-durable portion; and a time of flight (TOF) sensor, the TOF sensor being provided on the device a predetermined distance away from the HV line.

(51) The device according to any one of (1) to (50), wherein the TOF sensor is at a first side of the device in a radial direction and the HV line is at a second side of the device opposite the first side in the radial direction.

(52) The device according to any one of (1) to (51), wherein the TOF sensor is offset in a tangential direction from the HV line by about 180 degrees.

(53) The device according to any one of (1) to (52), further comprising a high voltage (HV) line to provide the high voltage from the durable portion to the semi-durable portion, wherein the user control interface includes a trigger switch to receive the manual input from the user, the trigger switch being at a first side of the device in a radial direction and the HV line being at a second side of the device opposite the first side in the radial direction.

(54) The device according to any one of (1) to (53), wherein the trigger switch is offset from the HV line by about 60 degrees to about 300 degrees in a tangential direction.

(55) The device according to any one of (1) to (54), further comprising a high voltage (HV) line to provide the high voltage from the durable portion to the semi-durable portion, wherein the durable portion includes a first plurality of undercuts and the semi-durable portion includes a second plurality of undercuts, each of the undercuts being located at respective longitudinal axes different from a longitudinal axis of the HV line.

(56) The device according to any one of (1) to (55), wherein the durable portion includes a detection switch to detect when the consumable portion is in contact with the durable portion.

(57) A durable portion according to any one of (1) to (56).

(58) A semi-durable portion according to any one of (1) to (56).

(59) A consumable portion according to any one of (1) to (56).

(60) A method comprising providing the device according to any one of (1) to (56).

(61) The method according to any one of (1) to (60), further comprising using the provided device.

(62) The method according to either (60) or (61), further comprising providing a spinning formulation for the solution, the spinning formulation being comprised of a volatile solvent selected from alcohol and ketone, polymer, and water, preferably the spinning formulation being comprised of ethanol, polymer, and water.

(63) A portable, hand-held device for electrospinning or electrospraying toward a deposit surface a predetermined solution formulated for the device, the device comprising: a durable portion; and a semi-durable portion configured to removably receive therein a consumable portion, wherein the semi-durable portion is configured to be removably coupled to the durable portion, wherein the durable portion is configured to provide a high voltage to the semi-durable portion and includes: a user control interface configured to receive manual input from a user to control a drive mechanism and application of the high voltage to the at least one electrode to create an electric field for application to the solution to electrospin or electrospray the solution from a nozzle of the semi-durable portion toward a deposit surface, wherein the semi-durable portion is configured to provide the high voltage to the at least one electrode and includes: the nozzle, which is configured to output the solution from a nozzle tip thereof, and the at least one electrode, which is inside the nozzle.

(64) The device according to (63), wherein the portion of the consumable overlapped by the semi-durable portion is at least 10% of a length of the consumable portion.

(65) The device according to (63) or (64), wherein the portion of the consumable overlapped by the semi-durable portion is between 10% and 50% of a length of the consumable portion.

(66) The device according to any one of (63) to (65), wherein when the consumable portion is removably received in the semi-durable portion and the semi-durable portion is not removably coupled to the durable portion, a portion of the consumable portion is exposed in a side view of the semi-durable portion.

(67) The device according to any one of (63) to (66), wherein the consumable portion is removable from the semi-durable portion when the semi-durable portion is removed from the durable portion.

(68) The device according to any one of (63) to (67), wherein the durable portion includes a light source.

(69) The device according to any one of (63) to (68), wherein the light source includes one or more light emitting diodes (LEDs).

(70) The device according to any one of (63) to (69), wherein the light source is in the form of a ring around a body of the durable portion.

(71) The device according to any one of (63) to (70), wherein the durable portion includes an electrically conductive portion on an outer surface thereof configured to allow for grounding of the device.

(72) The device according to any one of (63) to (71), wherein the electrically conductive portion is provided on a first side of the durable portion opposite a second side on which the user control interface is provided.

(73) The device according to any one of (63) to (72), further comprising a guide extending from an end of the durable portion configured to receive the semi-durable portion, the guide being configured to guide the semi-durable portion into proper coupling with the durable portion.

(74) The device according to any one of (63) to (73), further comprising the consumable portion, wherein the consumable portion includes a container configured to contain a predetermined maximum volume of the solution and output the solution to the at least one electrode of the semi-durable portion.

(75) The device according to any one of (63) to (74), wherein the semi-durable portion is configured to removably receive the consumable portion such that a sidewall of the semi-durable portion overlaps a portion of the consumable in a side view of the semi-durable portion.

(76) A portable, hand-held device for electrospinning or electrospraying toward a deposit surface a predetermined solution formulated for the device, the device comprising: a durable portion; and a semi-durable portion configured to removably receive therein a consumable portion, wherein the semi-durable portion is configured to be removably coupled to the durable portion, wherein the durable portion is configured to provide a high voltage to the semi-durable portion and includes: a user control interface configured to receive manual input from a user to control a drive mechanism and application of the high voltage to the at least one electrode to create an electric field for application to the solution to electrospin or electrospray the solution from a nozzle of the semi-durable portion toward a deposit surface, wherein the semi-durable portion is configured to provide the high voltage to the at least one electrode and includes: the nozzle, which is configured to output the solution from a nozzle tip thereof, and the at least one electrode, which is inside the nozzle, wherein the at least one electrode includes: a hollow tube, a conductive body portion surrounding the hollow tube such that a portion of the hollow tube extends from a first side of the conductive body portion, wherein the conductive body portion forms at least one secondary electrode, and wherein a second side of the conductive body opposite the first side corresponds to an outward-facing side of a second planar portion, the second side having one or more projections extending therefrom.

(77) The device according to (76), wherein the conductive body portion further includes a first planar portion spaced from the second planar portion in an axial direction of the hollow tube.

(78) The device according to (76) or (77), wherein the hollow tube extends from the second side of the conductive body portion.

(79) The device according to any one of (76) to (78), wherein the one or more projections include two projections, the projections being spaced apart from each other and symmetrically arranged on the outward-facing side of the second planar portion.

(80) The device according to any one of (76) to (79), wherein the at least one electrode includes an electrical connection arm that extends radially outward from the conductive body portion.

(81) The device according to any one of (76) to (80), wherein the durable portion includes a light source.

(82) The device according to any one of (76) to (81), wherein the light source includes one or more light emitting diodes (LEDs).

(83) The device according to any one of (76) to (82), wherein the light source is in the form of a ring around a body of the durable portion.

(84) The device according to any one of (76) to (83), wherein the durable portion includes an electrically conductive portion on an outer surface thereof configured to allow for grounding of the device.

(85) The device according to any one of (76) to (84), wherein the electrically conductive portion is provided on a first side of the durable portion opposite a second side on which the user control interface is provided.

(86) The device according to any one of (76) to (85), further comprising a guide extending from an end of the durable portion configured to receive the semi-durable portion, the guide being configured to guide the semi-durable portion into proper coupling with the durable portion.

(87) The device according to any one of (76) to (86), further comprising the consumable portion, wherein the consumable portion includes a container configured to contain a predetermined maximum volume of the solution and output the solution to the at least one electrode of the semi-durable portion.

(88) A portable, hand-held device for electrospinning or electrospraying toward a deposit surface a predetermined solution formulated for the device, the device comprising: a durable portion; and a semi-durable portion configured to removably receive therein a consumable portion, wherein the semi-durable portion is configured to be removably coupled to the durable portion, wherein the durable portion is configured to provide a high voltage to the semi-durable portion and includes: a user control interface configured to receive manual input from a user to control a drive mechanism and application of the high voltage to the at least one electrode to create an electric field for application to the solution to electrospin or electrospray the solution from a nozzle of the semi-durable portion toward a deposit surface, wherein the semi-durable portion is configured to provide the high voltage to the at least one electrode and includes: the nozzle, which is configured to output the solution from a nozzle tip thereof, and the at least one electrode, which is inside the nozzle, wherein the at least one electrode includes: a conductive hollow tube, a conductive body portion surrounding the conductive hollow tube such that a first portion of the conductive hollow tube extends from a first side of the conductive body portion and a second portion of the conductive hollow tube extends from a second side of the conductive body portion opposite the first side, and wherein the coupling of the semi-durable portion to the durable includes a combined electrical and mechanical connection including a connection rod extending from an end of the durable portion and into the semi-durable portion, the connection rod extending into the semi-durable portion and having an end thereof coupled to an elastic member.

(89) The device according to (88), further comprising a collar, the collar being rotatably coupled to the end of the durable portion so as to completely overlap the elastic member in a side view of the device.

(90) The device according to (88) or (89), wherein the elastic member overlaps a portion of the conductive hollow tube in a side view of the device.

(91) The device according to any one of (88) to (90), wherein the elastic member is arranged in the semi-durable portion, when the semi-durable portion is coupled to the durable portion, so as to contact or cause a contact to contact an arm of the conductive body portion, the contact forming an electrical conducting path.

(92) The device according to any one of (88) to (91), wherein the elastic member is radially inward of an outer sidewall of the semi-durable portion.

(93) The device according to any one of (88) to (92), wherein a longitudinal axis of the elastic member extends in a same direction as a longitudinal axis of the conductive hollow tube.

(94) The device according to any one of (88) to (93), wherein the at least one electrode includes an electrical connection arm that extends radially outward from the conductive body portion.

(95) The device according to any one of (88) to (94), wherein the durable portion includes a light source.

(96) The device according to any one of (88) to (95), wherein the light source includes one or more light emitting diodes (LEDs).

(97) The device according to any one of (88) to (96), wherein the light source is in the form of a ring around a body of the durable portion.

(98) The device according to any one of (88) to (97), wherein the durable portion includes an electrically conductive portion on an outer surface thereof configured to allow for grounding of the device.

(99) The device according to any one of (88) to (98), wherein the electrically conductive portion is provided on a first side of the durable portion opposite a second side on which the user control interface is provided.

(100) The device according to any one of (88) to (99), further comprising a guide extending from the end of the durable portion configured to receive the semi-durable portion, the guide being configured to guide the semi-durable portion into proper coupling with the durable portion.

(101) The device according to any one of (88) to (100), further comprising the consumable portion, wherein the consumable portion includes a container configured to contain a predetermined maximum volume of the solution and output the solution to the at least one electrode of the semi-durable portion.

Having now described embodiments of the disclosed subject matter, it should be apparent to those skilled in the art that the foregoing is merely illustrative and not limiting, having been presented by way of example only. Thus, although particular configurations have been discussed and illustrated herein, other configurations can be and are also employed. Further, numerous modifications and other embodiments (e.g., combinations, rearrangements, etc.) are enabled by the present disclosure and are contemplated as falling within the scope of the disclosed subject matter and any equivalents thereto. Features of the disclosed embodiments can be combined, rearranged, omitted, etc., within the scope of described subject matter to produce additional embodiments. Furthermore, certain features may sometimes be used to advantage without a corresponding use of other features. Accordingly, Applicant intends to embrace all such alternatives, modifications, equivalents, and variations that are within the spirit and scope of the present disclosure.

The invention claimed is:

1. A portable, hand-held device for electrospinning or electrospraying toward a deposit surface a predetermined solution formulated for the device, the device comprising:
 a durable portion; and
 a semi-durable portion configured to removably receive therein a consumable portion,
 wherein the semi-durable portion is configured to be removably coupled to the durable portion,
 wherein the durable portion is configured to provide a high voltage to the semi-durable portion and includes:
  a user control interface configured to receive manual input from a user to control a drive mechanism and application of the high voltage to at least one electrode to create an electric field for application to the solution to electrospin or electrospray the solution from a nozzle of the semi-durable portion toward the deposit surface,
- wherein the semi-durable portion is configured to provide the high voltage to the at least one electrode and includes:
  - the nozzle, which is configured to output the solution from a nozzle tip thereof, and
  - the at least one electrode, which is inside the nozzle,
- wherein the at least one electrode includes:
  - a hollow tube, and
  - a conductive body portion surrounding the hollow tube such that a portion of the hollow tube extends from a first side of the conductive body portion,
- wherein the conductive body portion forms at least one secondary electrode,
- wherein a second side of the conductive body opposite the first side corresponds to an outward-facing side of a second planar portion, the second side having one or more projections extending therefrom, and
- wherein an electrically conductive portion is provided on a first side of the durable portion opposite a second side on which the user control interface is provided.

2. The device according to claim 1, wherein a container of the consumable portion is sealed and configured to receive the at least one electrode.

3. The device according to claim 1,
- wherein the semi-durable portion includes a holder configured to hold a first end of the consumable portion when the consumable portion is removably coupled to the semi-durable portion, and
- wherein, the holder holds the first end of the consumable portion such that a second end of the consumable portion extends from the semi-durable portion.

4. The device according to claim 1, wherein, when the consumable portion is removably coupled to the semi-durable portion and the semi-durable portion is removably coupled to the durable portion, a first end of the consumable portion is inside the semi-durable portion and a second end of the consumable portion opposite the first end is inside the durable portion.

5. The device according to claim 1, wherein the consumable portion includes a cap, a container, and a piston.

6. The device according to claim 1, wherein the at least one electrode inside the nozzle includes a hollow tube portion and an extending portion that extends in a circumferential direction of the hollow tube portion.

7. The device according to claim 1, further comprising a high voltage (HV) line to provide the high voltage from the durable portion to the semi-durable portion, the HV line being surrounded by insulation of the semi-durable and/or insulation of the durable portion.

8. The device according to claim 1, further comprising a twist lock in the form of an about 10 to about 60 degrees twist lock, the twist lock including a collar rotatably coupled to the durable portion and configured to rotate about 10 to about 60 degrees to engage and disengage with the semi-durable portion when the semi-durable portion is removably coupled to the durable portion.

9. The device according to claim 1, further comprising a high voltage (HV) line to provide the high voltage from the durable portion to the semi-durable portion,
- wherein the user control interface includes a trigger switch to receive the manual input from the user, the trigger switch being at a first side of the device in a radial direction and the HV line being at a second side of the device opposite the first side in the radial direction.

10. The device according to claim 1, wherein the conductive body portion further includes a first planar portion spaced from the second planar portion in an axial direction of the hollow tube.

11. The device according to claim 1, wherein the one or more projections include two projections, the projections being spaced apart from each other and symmetrically arranged on the outward-facing side of the second planar portion.

12. A portable, hand-held device for electrospinning or electrospraying toward a deposit surface a predetermined solution formulated for the device, the device comprising:
a durable portion; and
a semi-durable portion configured to removably receive therein a consumable portion,
wherein the semi-durable portion is configured to be removably coupled to the durable portion,
wherein the durable portion is configured to provide a high voltage to the semi-durable portion and includes:
a user control interface configured to receive manual input from a user to control a drive mechanism and application of the high voltage to at least one electrode to create an electric field for application to the solution to electrospin or electrospray the solution from a nozzle of the semi-durable portion toward the deposit surface,
wherein the semi-durable portion is configured to provide the high voltage to the at least one electrode and includes:
the nozzle, which is configured to output the solution from a nozzle tip thereof, and
the at least one electrode, which is inside the nozzle,
wherein the at least one electrode includes:
a hollow tube, and
a conductive body portion surrounding the hollow tube such that a portion of the hollow tube extends from a first side of the conductive body portion,
wherein the conductive body portion forms at least one secondary electrode, and
wherein a second side of the conductive body opposite the first side corresponds to an outward-facing side of a second planar portion, the second side having one or more projections extending therefrom,
wherein the device further comprises a high voltage (HV) line to provide the high voltage from the durable portion to the semi-durable portion, the HV line being surrounded by insulation of the semi-durable and/or insulation of the durable portion.

13. The device according to claim 12, wherein a container of the consumable portion is sealed and configured to receive the at least one electrode.

14. The device according to claim 12,
wherein the semi-durable portion includes a holder configured to hold a first end of the consumable portion when the consumable portion is removably coupled to the semi-durable portion, and
wherein, the holder holds the first end of the consumable portion such that a second end of the consumable portion extends from the semi-durable portion.

15. The device according to claim 12, wherein, when the consumable portion is removably coupled to the semi-durable portion and the semi-durable portion is removably coupled to the durable portion, a first end of the consumable portion is inside the semi-durable portion and a second end of the consumable portion opposite the first end is inside the durable portion.

16. The device according to claim 12, wherein the consumable portion includes a cap, a container, and a piston.

17. The device according to claim 12, wherein the at least one electrode inside the nozzle includes a hollow tube portion and an extending portion that extends in a circumferential direction of the hollow tube portion.

18. The device according to claim 12, further comprising a twist lock in the form of an about 10 to about 60 degrees twist lock, the twist lock including a collar rotatably coupled to the durable portion and configured to rotate about 10 to about 60 degrees to engage and disengage with the semi-durable portion when the semi-durable portion is removably coupled to the durable portion.

19. The device according to claim 12, wherein the conductive body portion further includes a first planar portion spaced from the second planar portion in an axial direction of the hollow tube.

20. The device according to claim 12, wherein the one or more projections include two projections, the projections being spaced apart from each other and symmetrically arranged on the outward-facing side of the second planar portion.

* * * * *